(12) United States Patent
Sekhavat

(10) Patent No.: US 10,039,703 B2
(45) Date of Patent: Aug. 7, 2018

(54) COMPOSITION COMPRISING RESVERATROL AND MELATONIN FOR REDUCING HAIR LOSS AND/OR INCREASING HAIR REGROWTH

(71) Applicant: Triple Hair Inc., Dieppe, New Brunswick (CA)

(72) Inventor: Houfar Sekhavat, Dieppe (CA)

(73) Assignee: Triple Hair Inc., Dieppe, New Brunswick (CA)

( * ) Notice: Subject to any disclaimer, the term of this patent is extended or adjusted under 35 U.S.C. 154(b) by 0 days.

(21) Appl. No.: 15/502,970

(22) PCT Filed: May 5, 2016

(86) PCT No.: PCT/CA2016/000132
§ 371 (c)(1),
(2) Date: Feb. 9, 2017

(87) PCT Pub. No.: WO2017/004692
PCT Pub. Date: Jan. 12, 2017

(65) Prior Publication Data
US 2017/0231888 A1    Aug. 17, 2017

Related U.S. Application Data

(60) Provisional application No. 62/190,044, filed on Jul. 8, 2015.

(51) Int. Cl.
| | |
|---|---|
| A61K 31/405 | (2006.01) |
| A61K 8/49 | (2006.01) |
| A61Q 7/00 | (2006.01) |
| A61K 8/34 | (2006.01) |

(52) U.S. Cl.
CPC .............. A61K 8/492 (2013.01); A61K 8/347 (2013.01); A61Q 7/00 (2013.01)

(58) Field of Classification Search
USPC ....................................................... 514/415
See application file for complete search history.

(56) References Cited

U.S. PATENT DOCUMENTS

| | | |
|---|---|---|
| 4,746,674 A | 5/1988 | Pierpaoli et al. |
| 6,013,279 A | 1/2000 | Klett-Loch |
| 6,030,948 A | 2/2000 | Mann |
| 6,281,241 B1 | 8/2001 | Elsner |
| 6,818,226 B2 | 11/2004 | Reed et al. |
| 6,828,458 B2 | 12/2004 | Sovak et al. |
| 7,704,533 B2 | 4/2010 | Bruning et al. |
| 7,834,210 B2 | 11/2010 | Gupta |
| 8,017,645 B2 | 9/2011 | Schmid |
| 8,062,648 B2 | 11/2011 | Schmid |
| 8,163,311 B2 | 4/2012 | Bruning et al. |
| 8,470,833 B2 | 6/2013 | Hu et al. |
| 8,481,015 B2 | 7/2013 | Oblong et al. |
| 8,551,462 B2 | 10/2013 | Goldstein et al. |
| 8,591,874 B2 | 11/2013 | Oblong et al. |
| 8,802,117 B2 | 8/2014 | Morganti |
| 8,871,773 B2 | 10/2014 | Hu et al. |
| 8,877,762 B2 | 11/2014 | Hu et al. |
| 2009/0098069 A1 | 4/2009 | Vacca |
| 2011/0183016 A1 | 7/2011 | Mailland et al. |
| 2011/0195039 A1 | 8/2011 | Isaacs |
| 2012/0277249 A1 | 11/2012 | Anderson et al. |

FOREIGN PATENT DOCUMENTS

| | | |
|---|---|---|
| CA | 2 315 395 A1 | 7/1999 |
| CA | 2 339 231 A1 | 2/2000 |
| CA | 2 309 373 A1 | 11/2000 |
| CA | 2 309 413 A1 | 11/2000 |
| CA | 2 392 620 A1 | 6/2001 |
| CA | 2 206 530 C | 10/2001 |
| CA | 2 552 607 A1 | 7/2005 |
| CA | 2 558 150 A1 | 9/2005 |
| CA | 2 579 784 A1 | 3/2006 |
| CA | 2 608 031 A1 | 11/2006 |
| CA | 2 732 582 A1 | 2/2010 |
| CA | 2 765 284 A1 | 12/2010 |
| CA | 2 819 859 A1 | 6/2012 |
| CA | 2 838 646 A1 | 4/2013 |
| WO | WO 2000/048559 A2 | 8/2000 |
| WO | WO 2011/031990 A1 | 3/2011 |
| WO | WO 2013/078259 A2 | 5/2013 |
| WO | WO 2013/142295 A1 | 9/2013 |

OTHER PUBLICATIONS

Kwon et al., Journal of Pineal Research, 2011, 50(2): 110-123.*
International Search Report and Written Opinion dated Jul. 25, 201 from corresponding International Application No. PCT/CA2016/000132, 6 pages.
Uno, et al., "Effect of Latanoprost on Hair Growth in the Bald Scalp of the Stump-tailed Macacque: a Pilot Study", Abstract, *Acta Derm. Venereol*, 2002:82(1):7-12 (1 page).
T.W. Fischer et al., "Melatonin Increases Anagen Hair Rate in Women With Androgenetic Alopecia or Diffuse Alopecia: Results of Randomized Controlled Trials," British Journal of Dermatology, pp. 341-345, 2004, 5 pages.
T.W. Fischer et al., "Topical Melatonin for Treatment of Androgenetic Alopecia," Int. J. Trichology, Oct.-Dec. 2012, 4(4), pp. 236-245, 2012, 13 pages.
T. Kiskova et al., "A Combination of Resveratrol and Melatonin Exerts Chemopreventive Effects in N-methyl-N-nitrosourea-Induced Rat Mammary Carcinogenesis," European Journal of Cancer Prevention, vol. 21, No. 2, pp. 163-170, 2012, 8 pages.
http://www.medicalwellnesscenter.com, Jun. 2013 (10 pages), including http://xenicalwtloss.hypermart.net/MINOXIDILSHAMPOOHairLossPrescriptionINDEX . . . (Jun. 2013) (1 page), total 11 pages.

(Continued)

*Primary Examiner* — Rei Tsang Shiao
(74) *Attorney, Agent, or Firm* — Flaster/Greenberg P.C.

(57) ABSTRACT

The invention relates to a composition comprising 0.01% to 15% resveratrol and 0.01% to 15% of melatonin. In a preferred embodiment, the composition comprises 5% resveratrol and 0.1% melatonin. The invention also relates to the use of the said composition to reduce hair loss and/or increase regrowth of hair in a human subject.

14 Claims, 54 Drawing Sheets

(56) References Cited

OTHER PUBLICATIONS

Levy, et al. "Female Pattern Alopecia: Current Perspectives", *Int. J. Women's Health*, 2013, 5:541-556, Aug. 2013, 19 pages.
GlaxoSmithKline, "GlaxoSmithKline Publishes Japanese Dutasteride Hair Loss Study Results", Sep. 2014, 3 pages.
http://www.hairloss-research.org/UpdateResveratrol11-07.html, "MPB research, Italian Patent Details Hair Growth Effects of Resveratrol/Curcumin Combination," Nov. 2014, 3 pages.
http://www.hairlosstalk.com/interact/showthread.php/61517-Resveratrol/Curcumin-for-hair . . . , "Hair Loss Talk, Thread: Resveratrol/Curcumin For Hair Loss," Nov. 2014, 3 pages.
http://www.belgraviacentre.com, Belgravia Centre "Japan Delays Dutasteride Drug for Male Pattern Hair Loss", retrieved May 2016, 8 pages.
http://hairlosscure2020.com, "The End of Hair Loss and Balding by 2020," Brief Items of Interest, May 2016, 9 pages.
Hamishehkar et al., "Histological Assessment of Follicular Delivery of Flutamide by Solid Lipid Nanoparticles: Potential Tool for the Treatment of Androgenic Alopecia," *Drug Dev. Ind. Pharm.* Jun. 2016;42(6):846:53, 2 pages.
http://www.resveratrolnews.com/attention-all-balding-males-resveratrol-to-your-rescue/5201, B. Sarch, "Reseveratrol News, Attention All Balding Males: Resveratrol to Your Rescue," Jun. 2016, 2 pages.
Candelario-Jalil et al., "Resveratrol Potently Reduces Prostaglandin E2 Production and Free Radical Formation in Lipopolysaccharide-Activated Primary Rat Microglia," J. Neuroinflammation 4(25) (Oct. 10, 2007) (12 pages).
Yip et al., "Gene-Wide Association Study Between the Aromatase Gene (CYP19A1) and Female Pattern Hair Loss," British Journal of Dermatology 161(2), p. 289-294 (Apr. 29, 2009) (7 pages).
Ndiaye et al., "The Grape Antioxidant Resveratrol for Skin Disorders: Promise, Prospects, and Challenges," Arch Biochem Biophys. 508(2), p. 164-170 (Apr. 15, 2011) (18 pages).
Garza et al., "Prostaglandin D2 Inhibits Hair Growth and is Elevated in Bald Scalp of Men with Androgenetic Alopecia," Sci. Transl. Med. 4(126) (Mar. 21, 2012) (21 pages).
Fischer et al., "Topical Melatonin for Treatment of Androgenetic Alopecia," Int. J. Trichology 4(4), p. 236-245 (Oct.-Dec. 2012) (21 pages).
Chottanapund et al., "Anti-Aromatase Effect of Resveratrol and Melatonin on Hormonal Positive Breast Cancer Cells Co-Cultured with Breast Adipose Fibroblasts," Toxicol. In Vitro 28(7), p. 1215-1221 (Oct. 2014) (7 pages).
Canadian Office Action from Canadian counterpart application No. 2,958,794, dated Jan. 11, 2018 (3 pages).

* cited by examiner

COMPOSITION COMPRISING RESVERATROL AND MELATONIN FOR REDUCING HAIR LOSS AND/OR INCREASING HAIR REGROWTH

BACKGROUND OF THE INVENTION

Field of the Invention

The inventor has discovered that a composition comprising resveratrol and melatonin shows improved properties in terms of reducing hair loss and increasing hair regrowth when compared to conventional therapies, such as the topical application of a solution of 5% minoxidil.

Description of Related Art

Androgenetic alopecia (AGA) is hair loss (at scalp level) caused by the thinning of hair follicles. It is very common in men between the age of 19 and 70 years. Notably, more than 50% of Caucasian men in their fifties are affected by it. Women's hair loss mostly becomes an issue after menopause.

Individuals affected by androgenetic alopecia (AGA) show a diminution of their self-esteem that can effect negatively many facets of their lives. The inventor has discovered that a composition for topical administration comprising resveratrol and melatonin is effective in reducing hair loss and increasing hair regrowth.

There are several hair loss prevention products on the market. By way of example, minoxidil has been in use since the 1990s in topical form at 2% concentration (without prescription) and at 3% and 5% concentration (with prescription). While studies demonstrate the efficiency of 5% minoxidil over the 2% concentration, minoxidil is less than 40% effective in promoting regrowth of the hair. Minoxidil is considered the topical gold standard available for treatment of hair loss.

Another hair loss prevention product is finasteride. It is administered orally usually at a dosage of 1 mg/day. There are a number of side effects associated with the administration of finasteride including lowered libido, impotence, ejaculation disorders, allergic reactions, testicular pain, male infertility, male breast cancer and depression. At higher concentrations (5 mg), finasteride can cause benign prostate hyperplasia.

BRIEF SUMMARY OF THE INVENTION

The inventor has discovered that a composition comprising resveratrol and melatonin for topical application to the scalp reduces hair loss and increases hair regrowth. Such a composition shows superior improvements to those seen for each of the components of the composition taken individually and to a composition comprising 5% minoxidil and the results obtained to date suggest that the improvements may be superior to those of the sum of the said components.

The invention relates to a composition comprising 0.01% to 15% resveratrol and 0.01% to 15% of melatonin. In another embodiment, the composition comprises 5% resveratrol and 0.1% melatonin. The invention also relates to the use of a composition comprising 0.01% to 15% resveratrol and 0.01% to 15% of melatonin to reduce hair loss and/or increase regrowth of hair in a human subject.

BRIEF DESCRIPTION OF THE SEVERAL VIEWS OF THE DRAWINGS

The FIGS. 1A to 1C are a series of photographs showing the scalp of participant 1 prior to treatment on the first day of month one (FIG. 1A) and at months three (FIG. 1B) and six (FIG. 1C) of a six month treatment with a solution of 5% resveratrol and 0.1% melatonin.

DETAILED DESCRIPTION OF THE INVENTION

Figure 1A:

The invention relates to a composition comprising resveratrol and melatonin which shows improved properties for the reduction of hair loss and for the increase of hair regrowth in human subjects when compared to minoxidil.

Resveratrol is a natural product in topical form derived from polygonum multiflorum, an Asian cane.

Melatonin is mostly used to treat insomnia. The FDA classifies melatonin as a dietary supplement.

An exemplary composition of the invention comprises 0.01% to 15% resveratrol and 0.01% to 15% of melatonin. In another embodiment, the composition comprises 5% resveratrol and 0.01% melatonin.

In order to demonstrate the improved properties of a composition suitable for topical application comprising resveratrol and melatonin, the composition was compared to compositions comprising 5% minoxidil only, 0.1% melatonin only and 5% resveratrol only. The various compositions were prepared as follows.

Example 1

Preparation of Composition Comprising Resveratrol and Melatonin

The composition comprises 5% resveratrol and 0.1% melatonin as the active ingredients and propylene glycol and absolute ethyl alcohol as non-active ingredients. The alcohol also serves as the final preservative in the composition.

Various modifications for the preparation of the composition of the invention will be apparent to the skilled worker. Furthermore, other pharmaceutically acceptable additives such as suspending agents, emulsifying agents, non-aqueous vehicles and preservatives can be added. The techniques for the preparation of these compositions are well known in the art and reference may be had to Remington's Pharmaceutical Sciences, 18th edition, Mack Publishing Co., Easton, Pa., USA 18042.

Example 2

Preparation of Composition Comprising Minoxidil

A composition comprising 5% minoxidil was prepared. Absolute ethyl alcohol was mixed with propylene glycol and heated to 55° to 65° C. The minoxidil powder was added to the alcohol/propylene glycol mixture. Ethoxy diglycol was added and the solution was stirred. The final solution was brought to volume with absolute ethyl alcohol to obtain a solution comprising 5% minoxidil.

Example 3

Preparation of Composition Comprising Resveratrol

A composition comprising 5% resveratrol was also prepared. Absolute ethyl alcohol was mixed with propylene glycol. Resveratrol was added to the alcohol/propylene glycol mixture to obtain a solution having a concentration of 5% resveratrol. Absolute ethyl alcohol also serves the function of preservative.

Example 4

Preparation of Composition Comprising Melatonin

A solution comprising 0.1% melatonin was prepared. Absolute ethyl alcohol was mixed with propylene glycol. The melatonin was added to the alcohol/propylene glycol mixture. The final solution was brought to volume with absolute ethyl alcohol in order to obtain a solution having a concentration of 0.01% melatonin. The absolute ethyl alcohol also serves the function of preservative in this composition.

Example 5

Treatment of Participants with Composition of Invention and Comparators—Analysis and Measurements Each participant had androgenetic alopecia.

For each participant, the distance between the base of the nose and the middle of the hair crown was noted, as well as the distance separating the most distal part of the helix and the hair crown. A square area of two centimeters by two centimeters was measured around the middle point of the hair crown (marked by a washable felt crayon).

The participants were seen at monthly intervals over a six-month period and their hair was analysed in the manner described above.

Results

A. Treatment with Composition Comprising Resveratrol and Melatonin

Each participant first had his hair analysed as described above. Following the first analysis, each participant was provided with a solution comprising 5% resveratrol, and 0.1% melatonin prepared as described in Example 1 above. The participants applied 1 ml to the scalp, once a day after cleansing. The 1 ml was applied as 10 metered dose sprays of 0.1 ml.

The results for six participants are provided. Particulars of each participants are provided in Table 1 below. All six participants had androgenic alopecia, as did the participants of their comparator groups.

TABLE 1

| Participant | Gender | Age |
| --- | --- | --- |
| 1 | Male | 38 |
| 2 | Male | 38 |
| 3 | Male | 36 |
| 4 | Male | 45 |
| 5 | Male | 32 |
| 6 | Male | 57 |

Figure 1B:
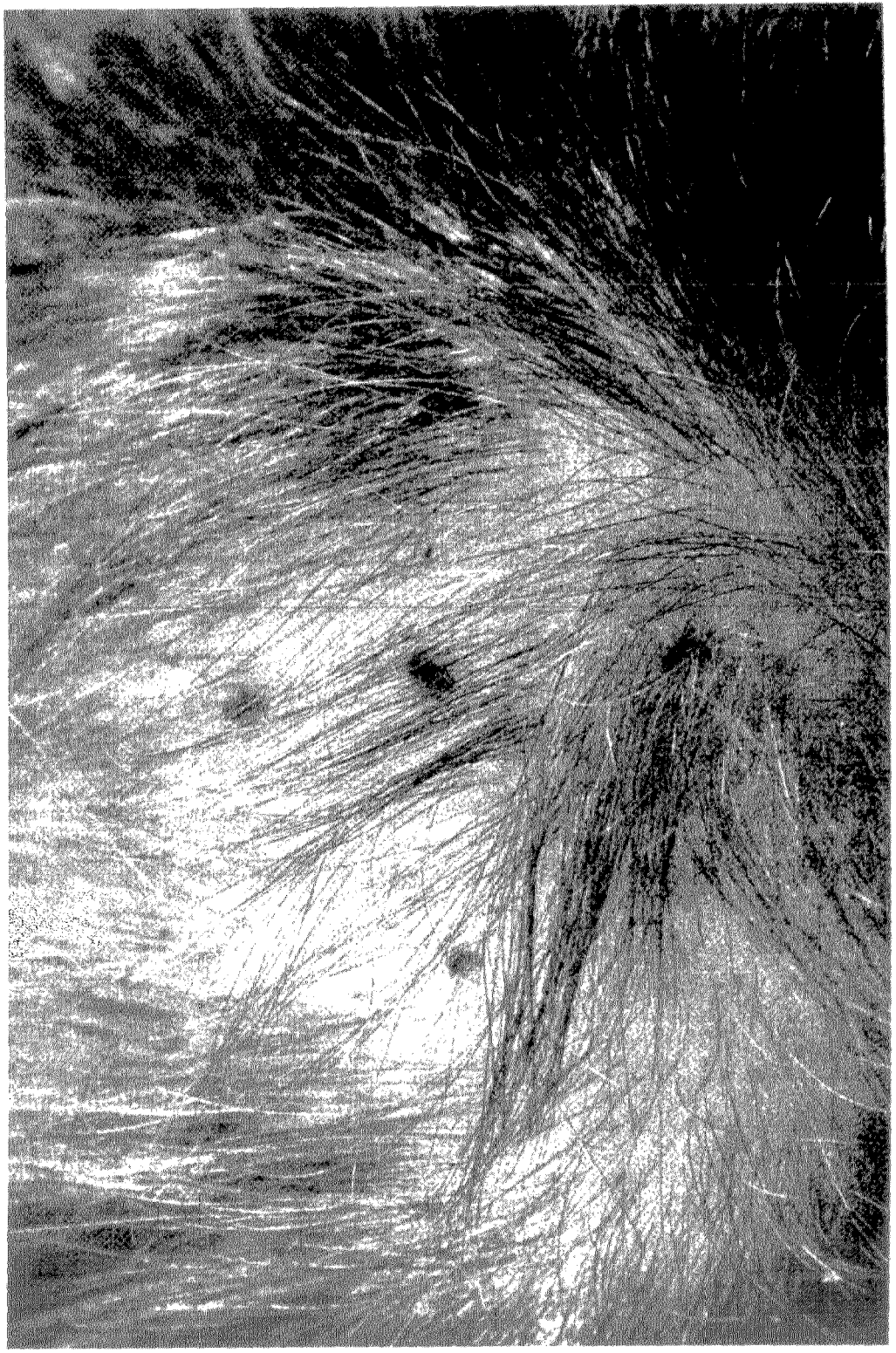
Figure 1C:
Figure 2A:
FIGS. 2A to 2C are a series of photographs showing the scalp of participant 2 prior to treatment on the first day of month one (FIG. 2A) and at months three (FIG. 2B) and six (FIG. 2C) of a six month treatment with a solution of 5% resveratrol and 0.1% melatonin.
Figure 2B:
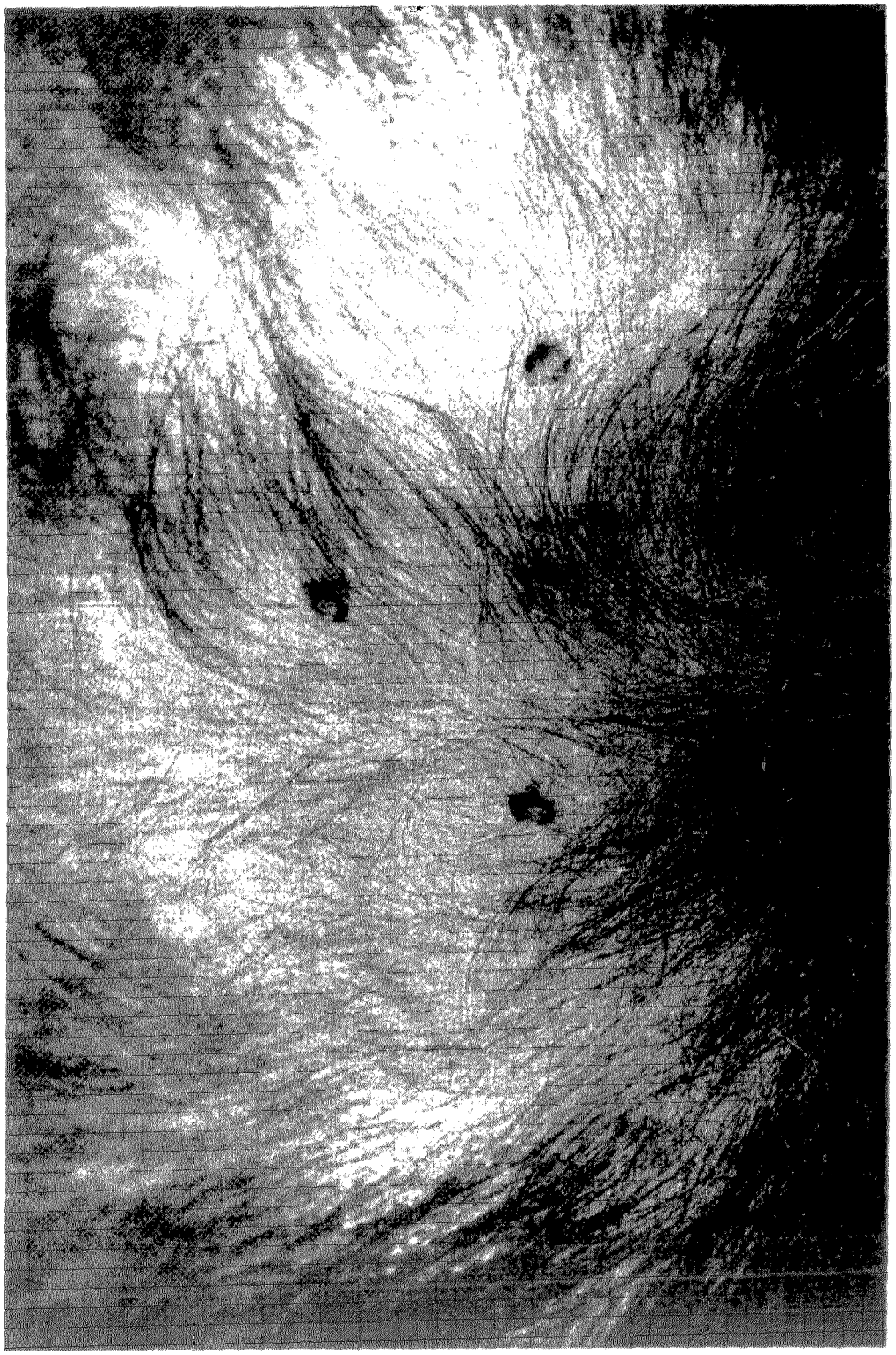
Figure 2C:
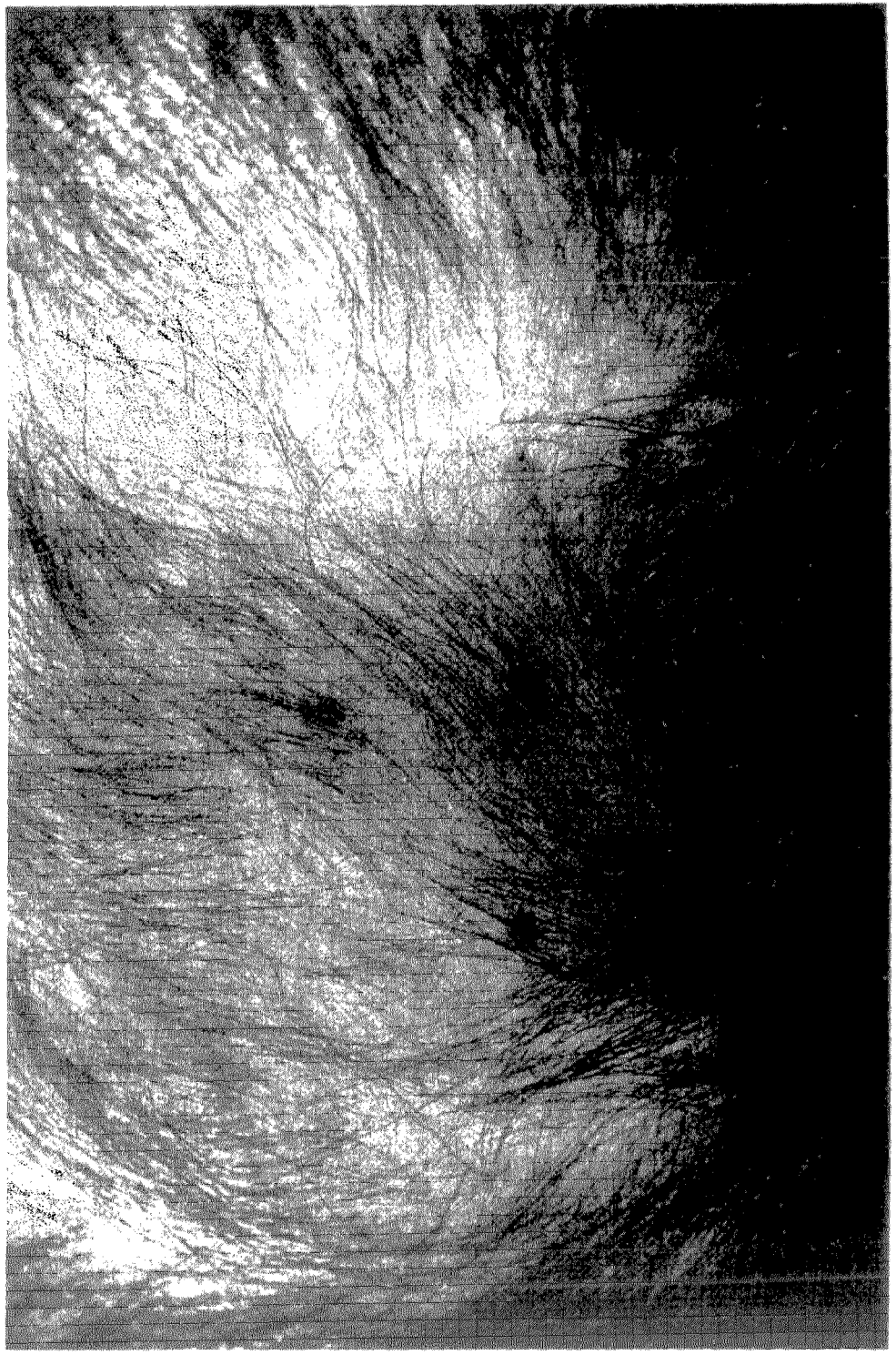
Figure 3A:
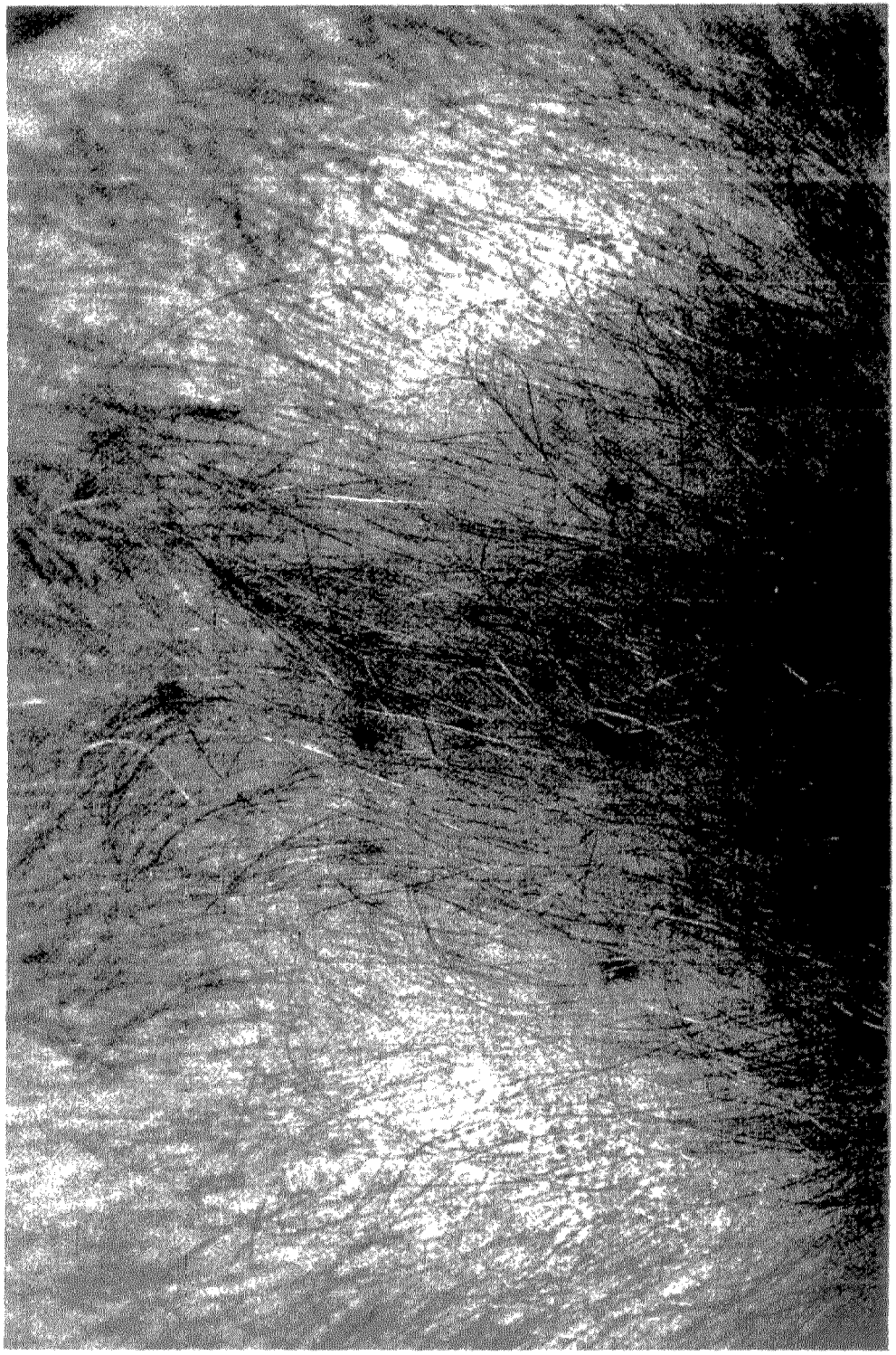
FIGS. 3A to 3C are a series of photographs showing the scalp of participant 3 prior to treatment on the first day of month one (FIG. 3A) and at months three (FIG. 3B) and six (FIG. 3C) of a six month treatment with a solution of 5% resveratrol and 0.1% melatonin.
Figure 3B:
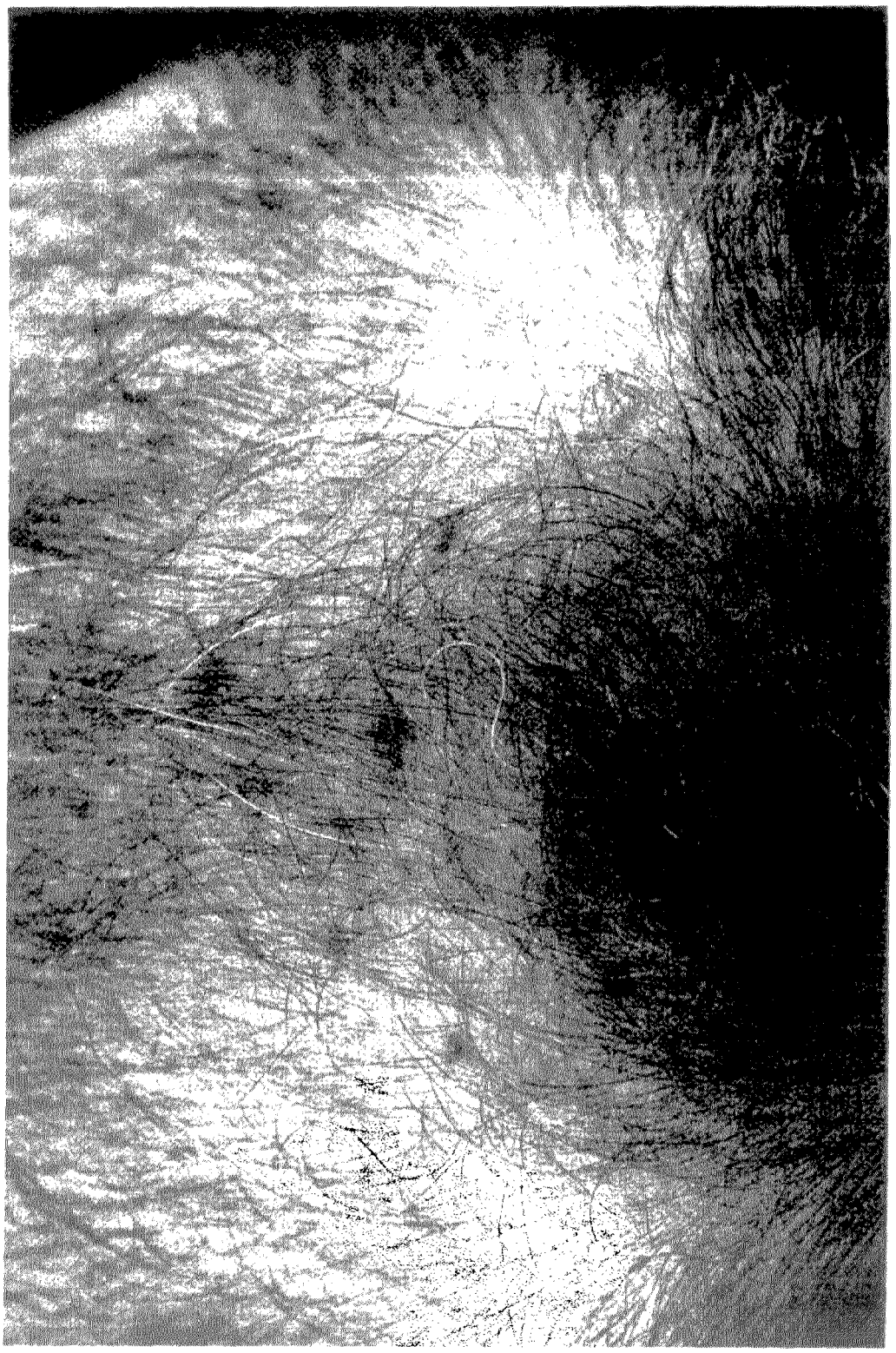
Figure 3C:
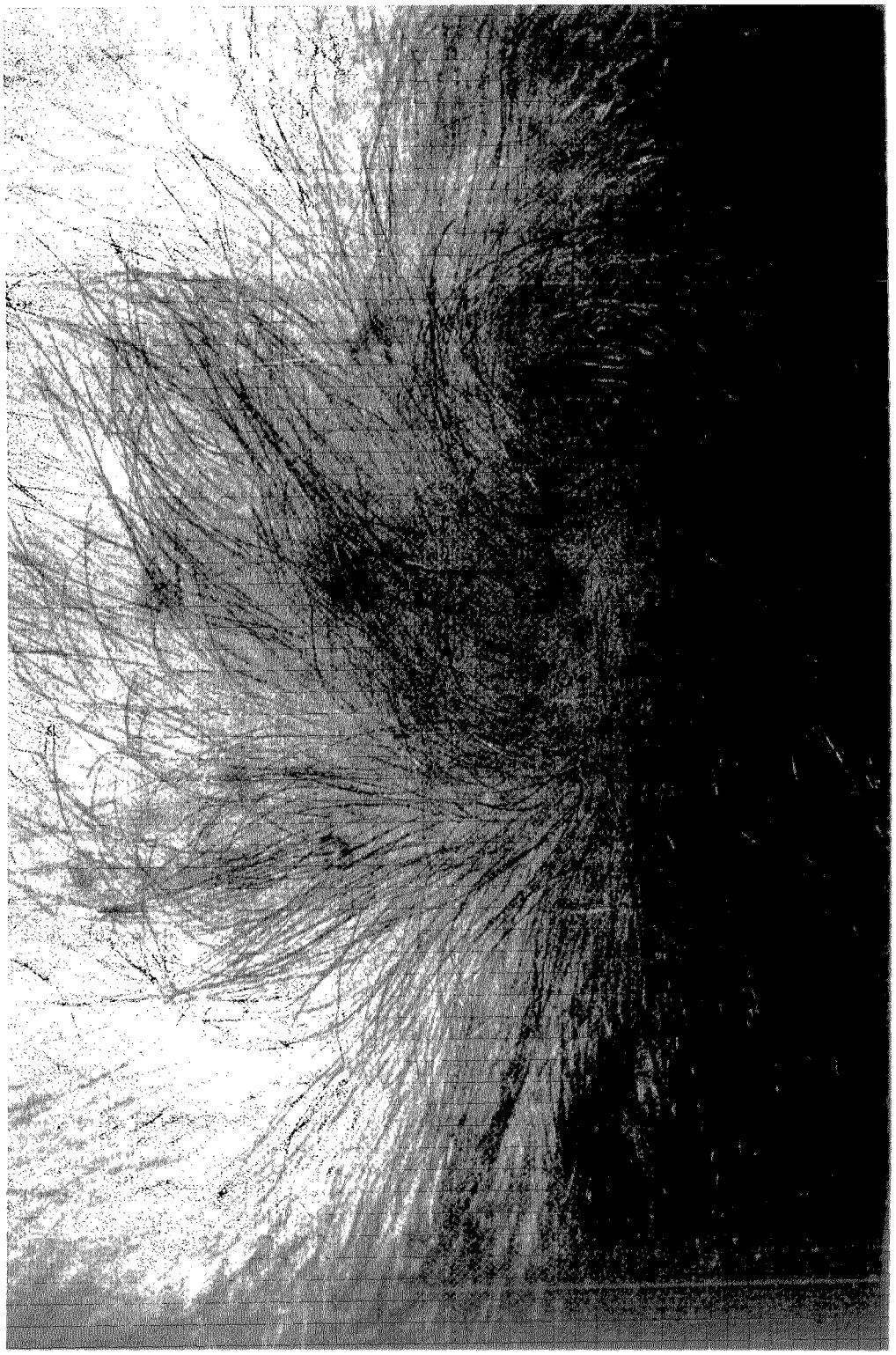
Figure 4A:
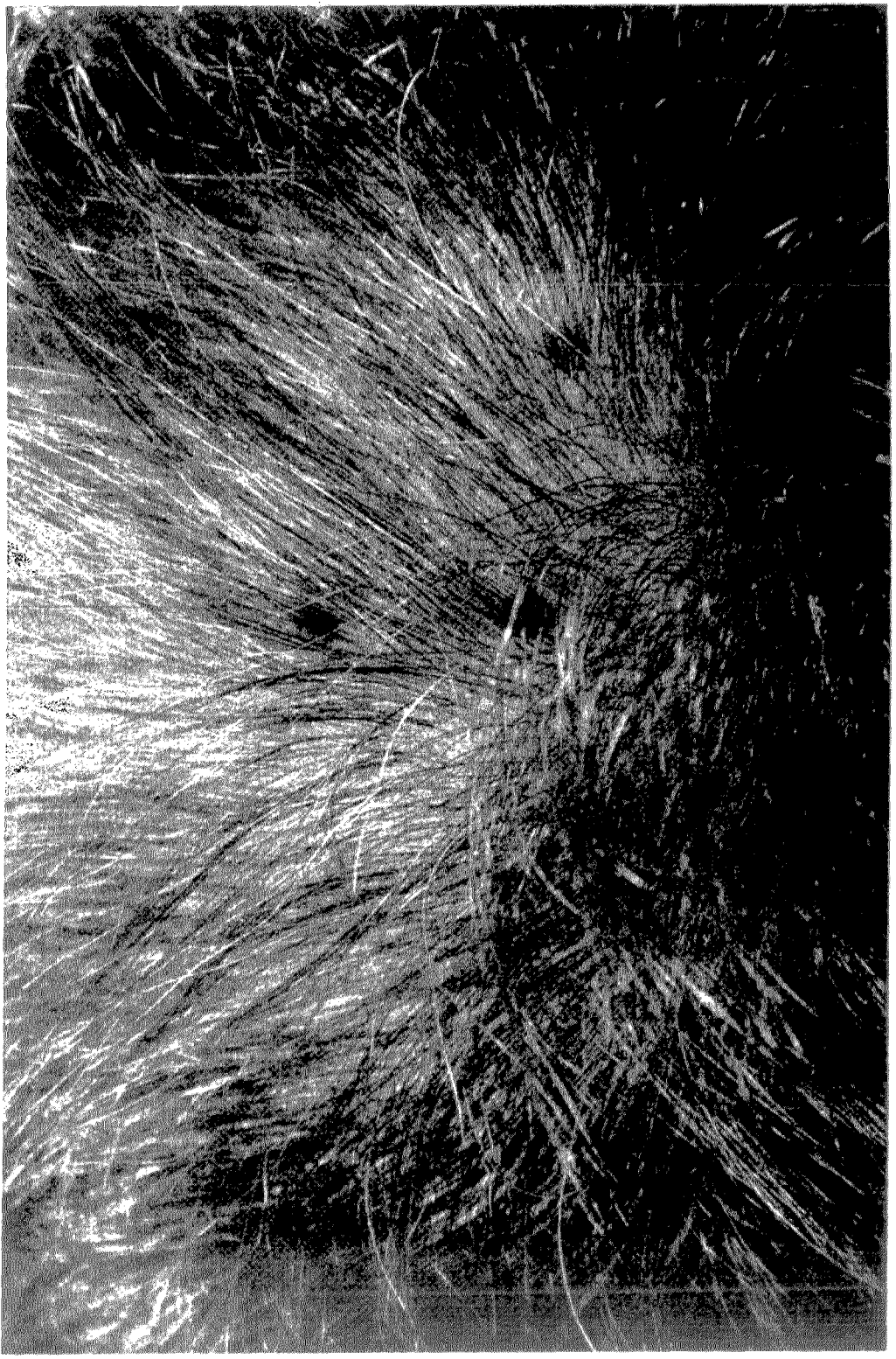
FIGS. 4A to 4C are a series of photographs showing the scalp of participant 4 prior to treatment on the first day of month one (FIG. 4A) and at months three (FIG. 4B) and six (FIG. 4C) of a six month treatment with a solution of 5% resveratrol and 0.1% melatonin.
Figure 4B:
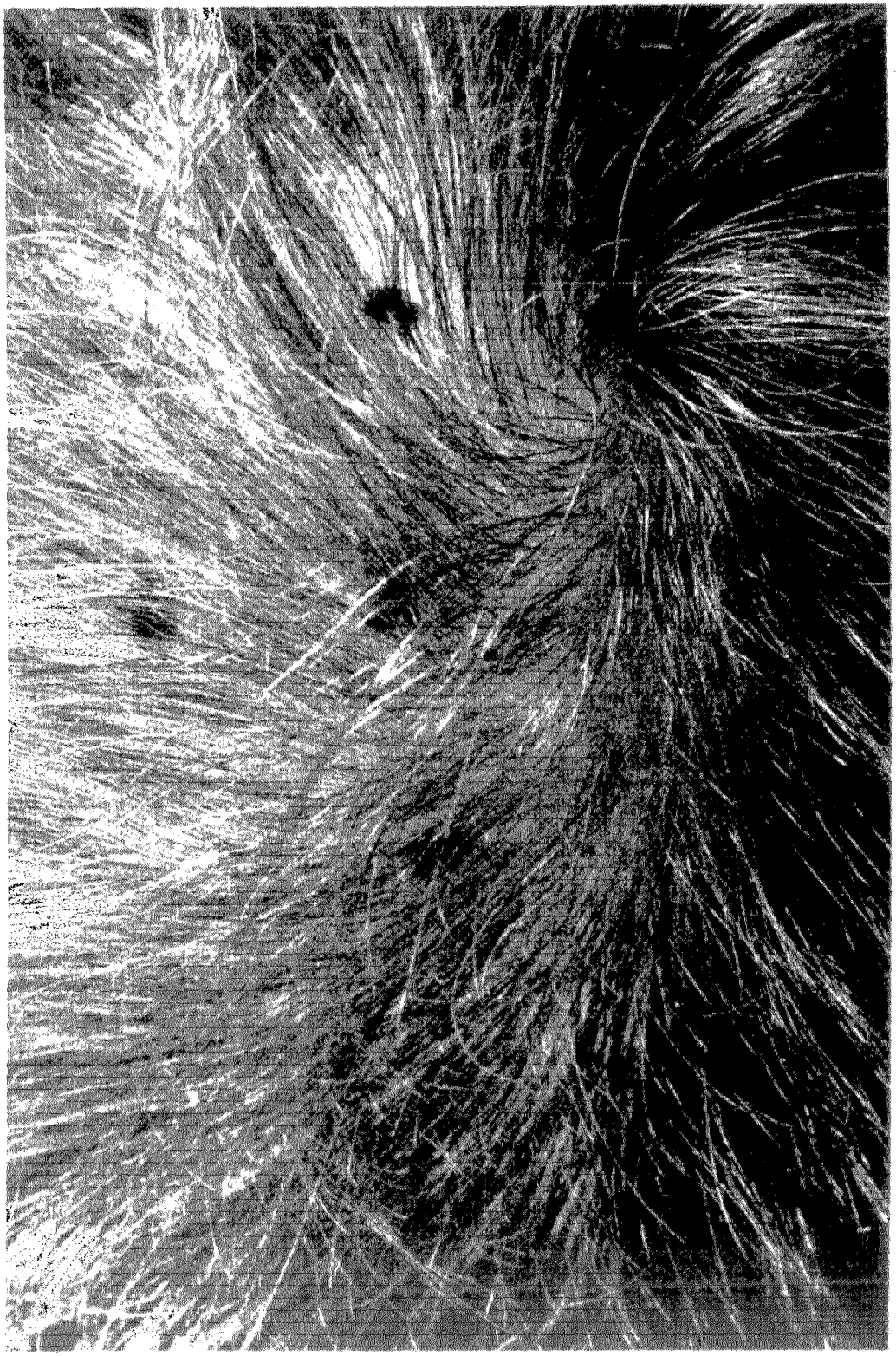
Figure 4C:
Figure 5A:
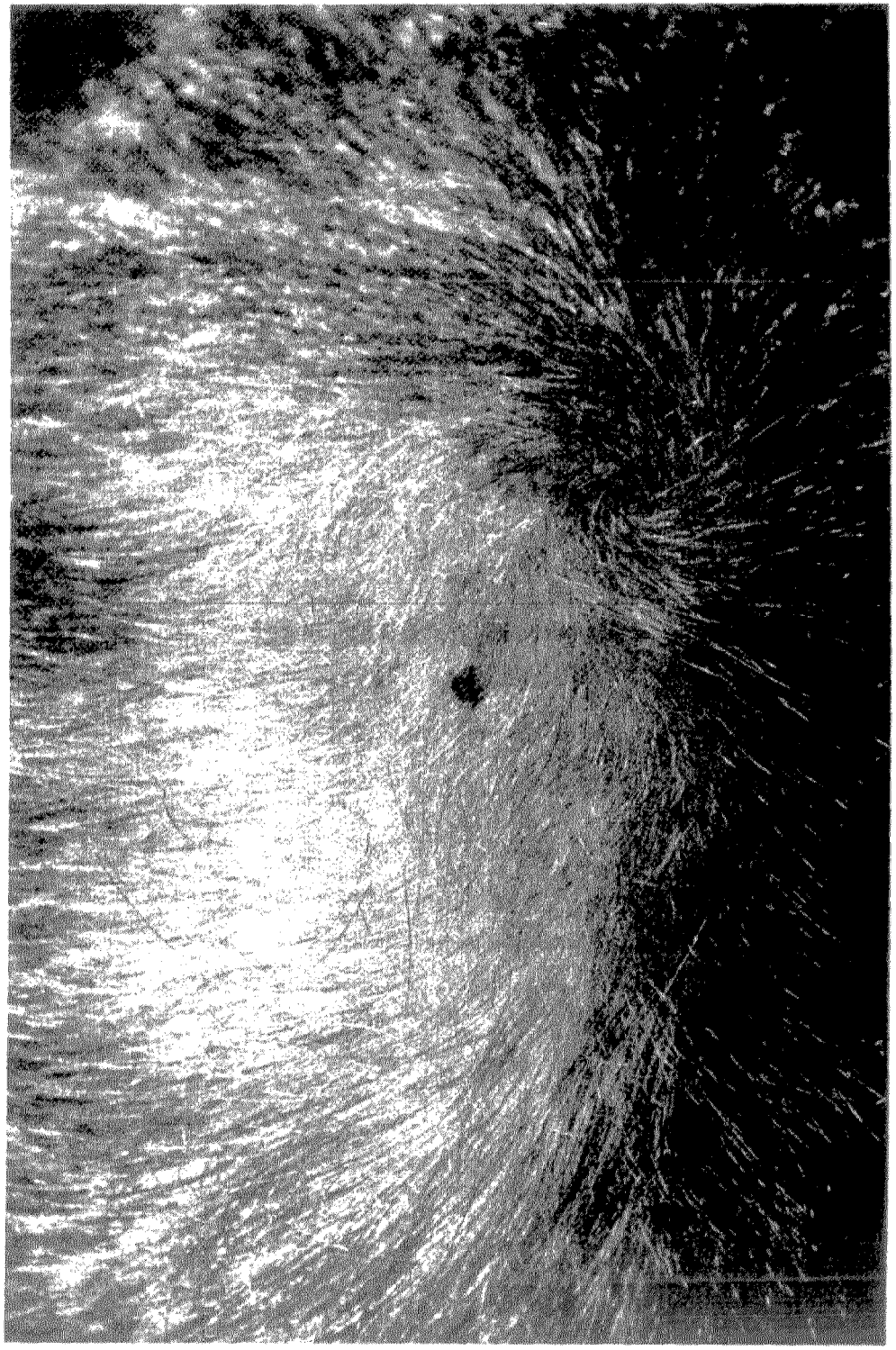
FIGS. 5A to 5C are a series of photographs showing the scalp of participant 5 prior to treatment on the first day of month one (FIG. 5A) and at months three (FIG. 2B) and six (FIG. 5C) of a six month treatment with a solution of 5% resveratrol and 0.1% melatonin.
Figure 5B:
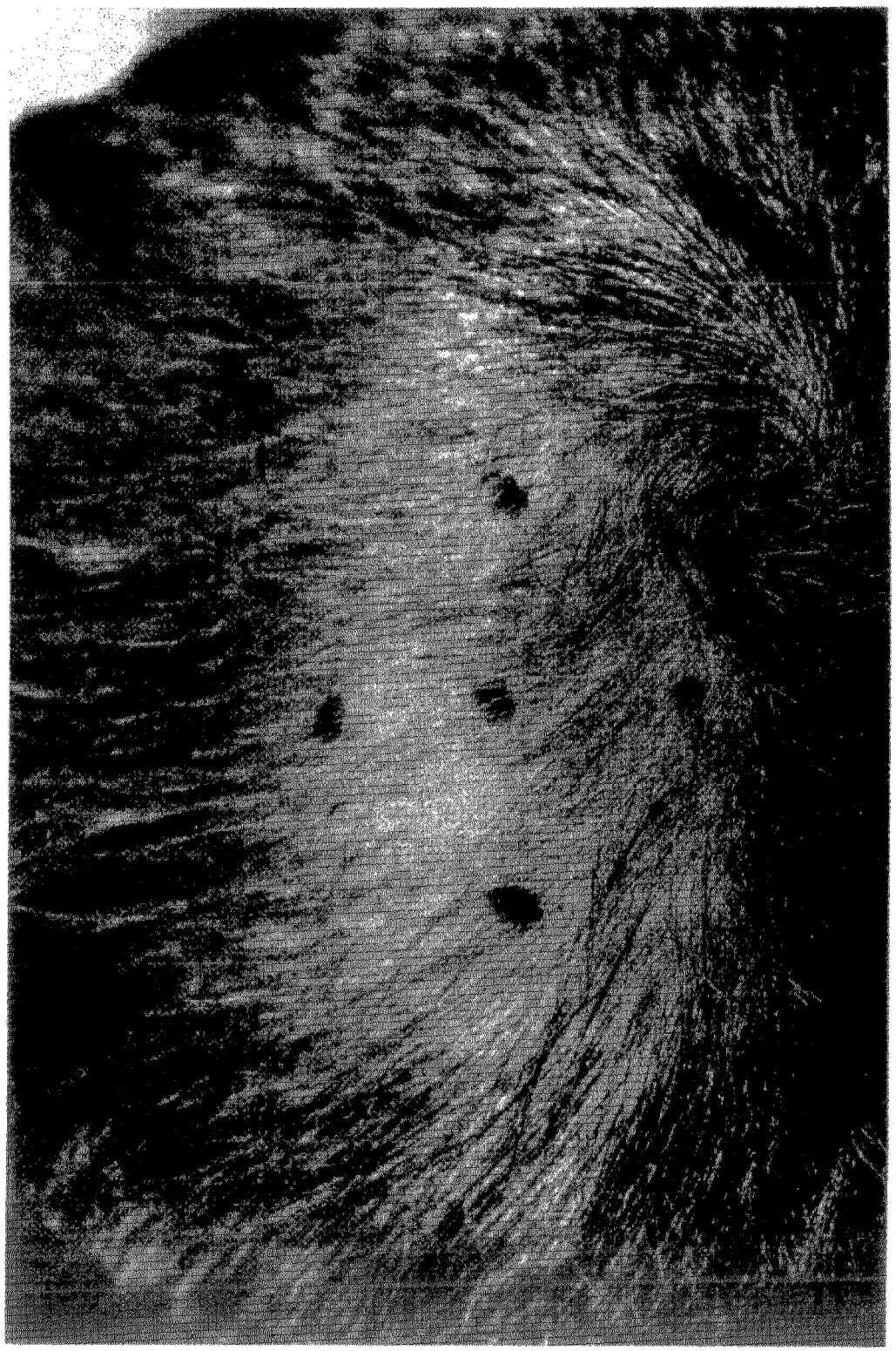
Figure 5C:
Figure 6A:
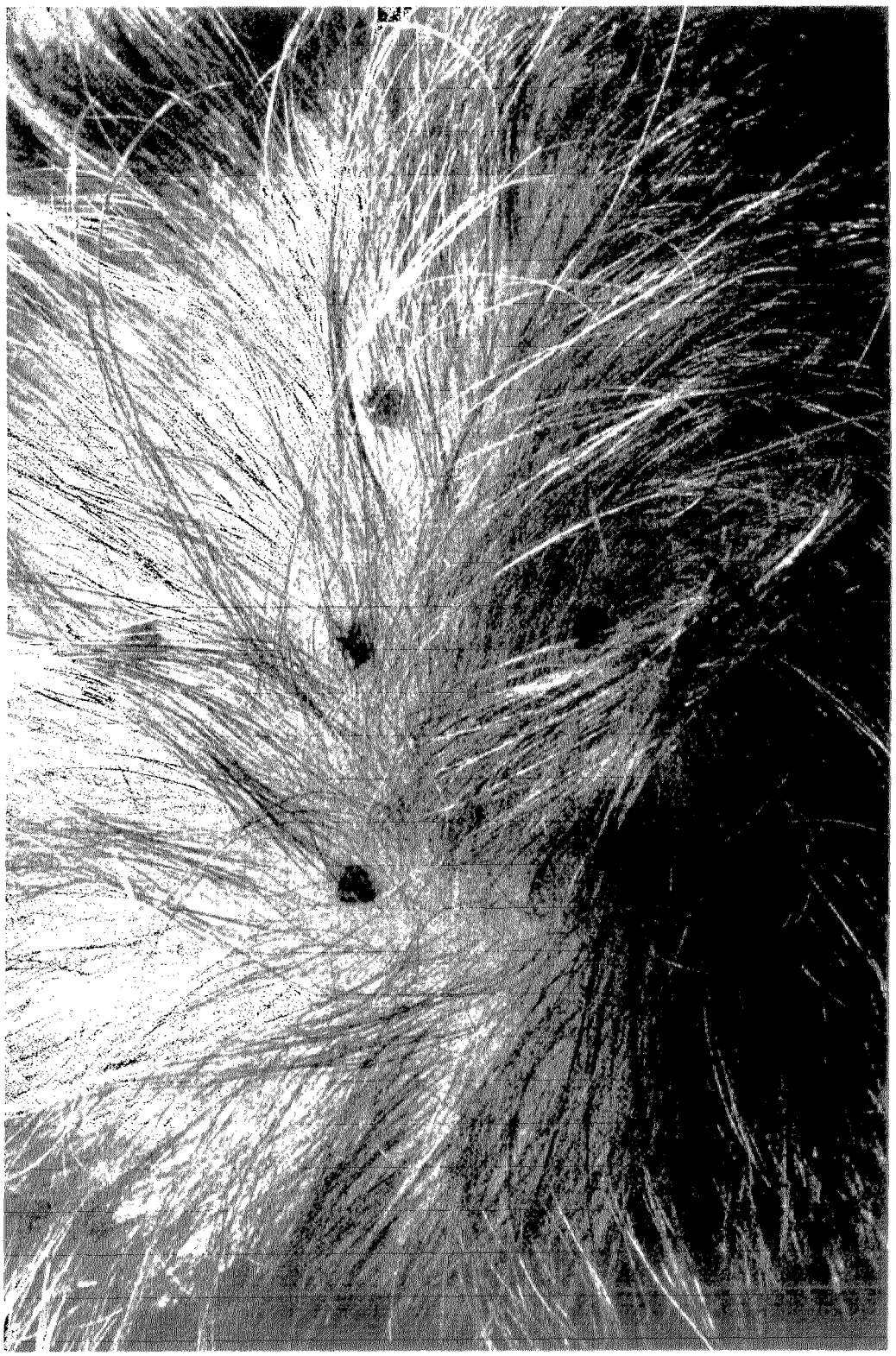
FIGS. 6A to 6C are a series of photographs showing the scalp of participant 6 prior to treatment on the first day of month one (FIG. 6A) and at months three (FIG. 6B) and six (FIG. 6C) of a six month treatment with a solution of 5% resveratrol and 0.1% melatonin.
Figure 6B:
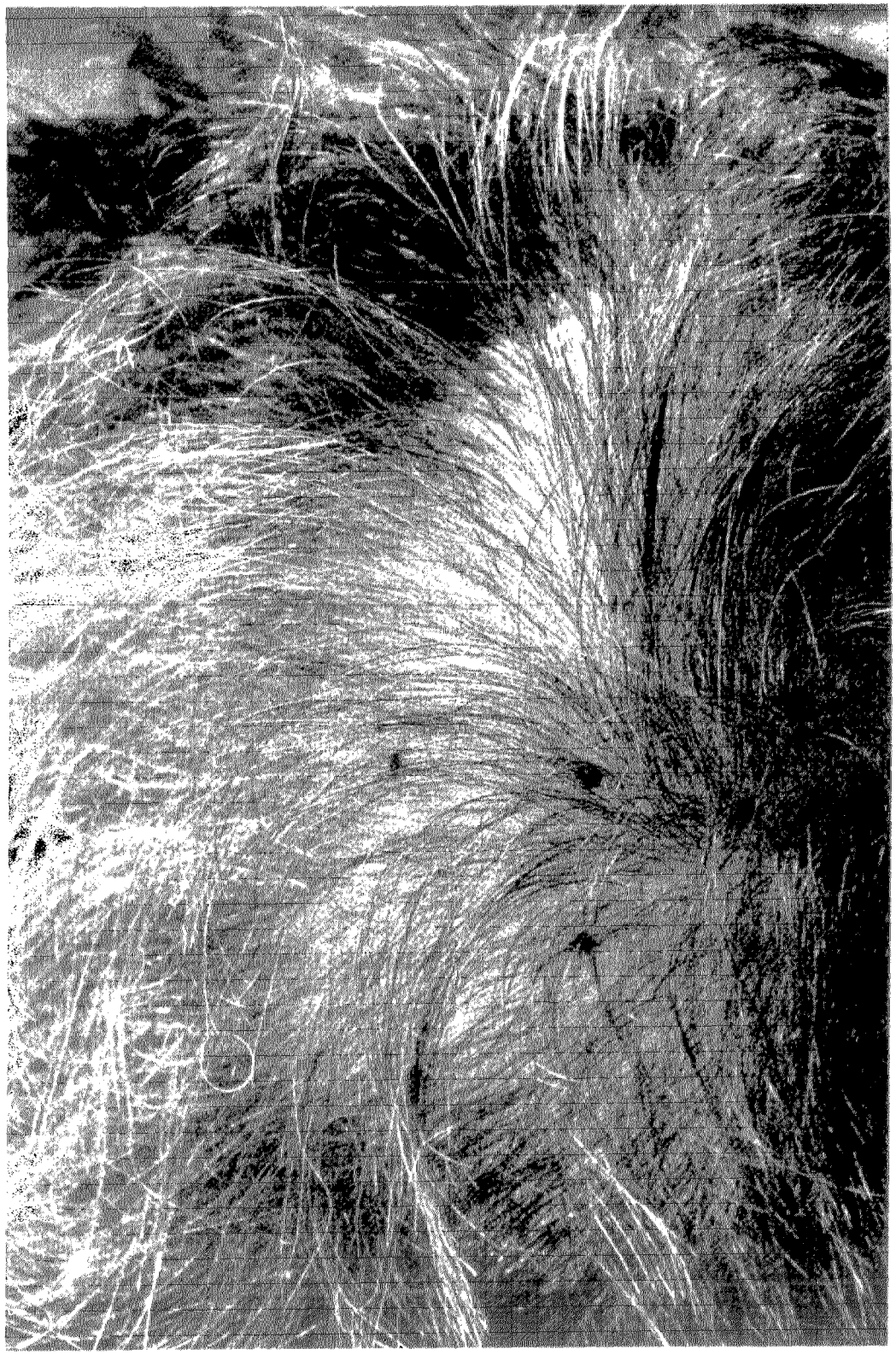
Figure 6C:
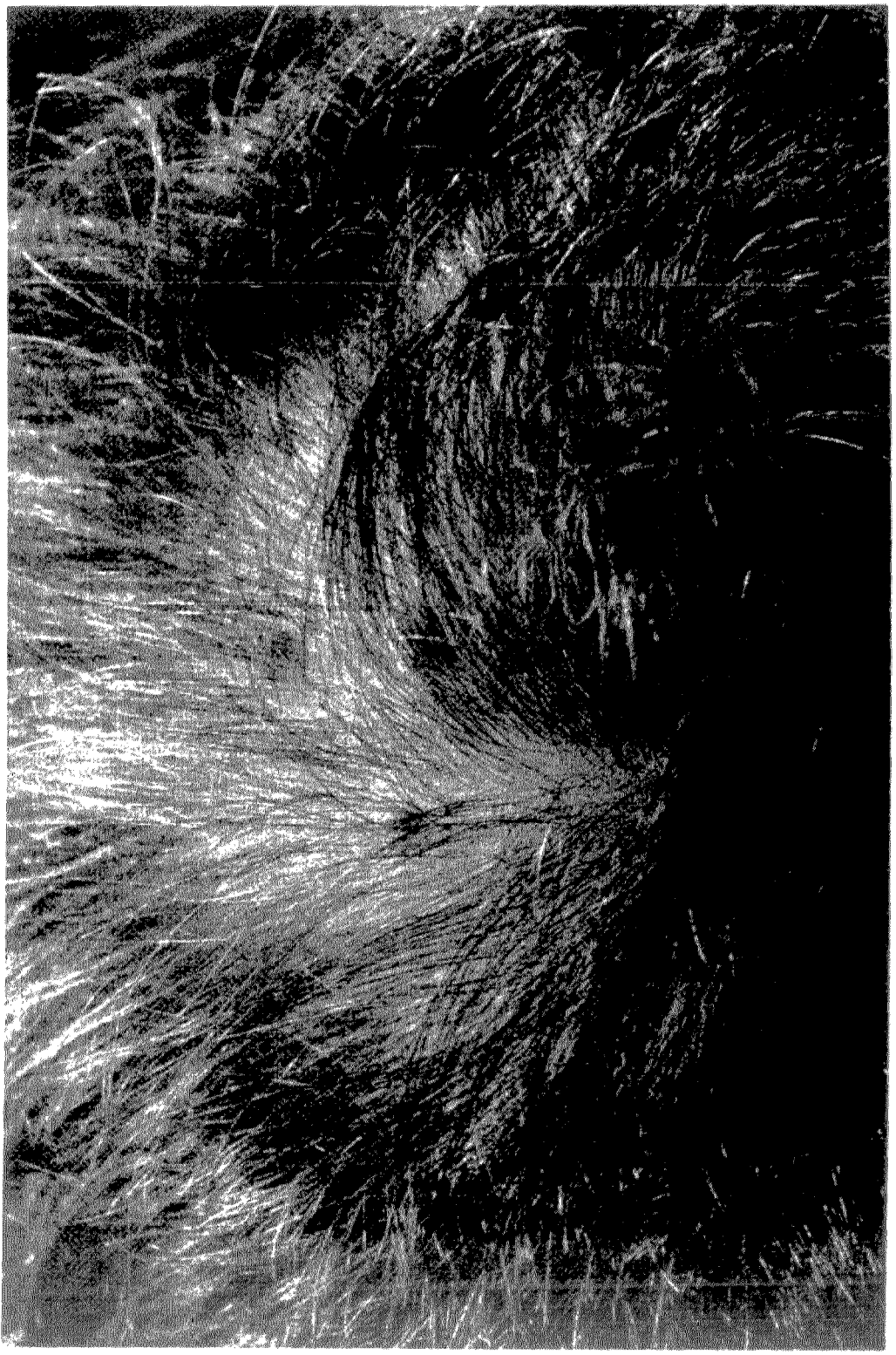
Figure 7A:
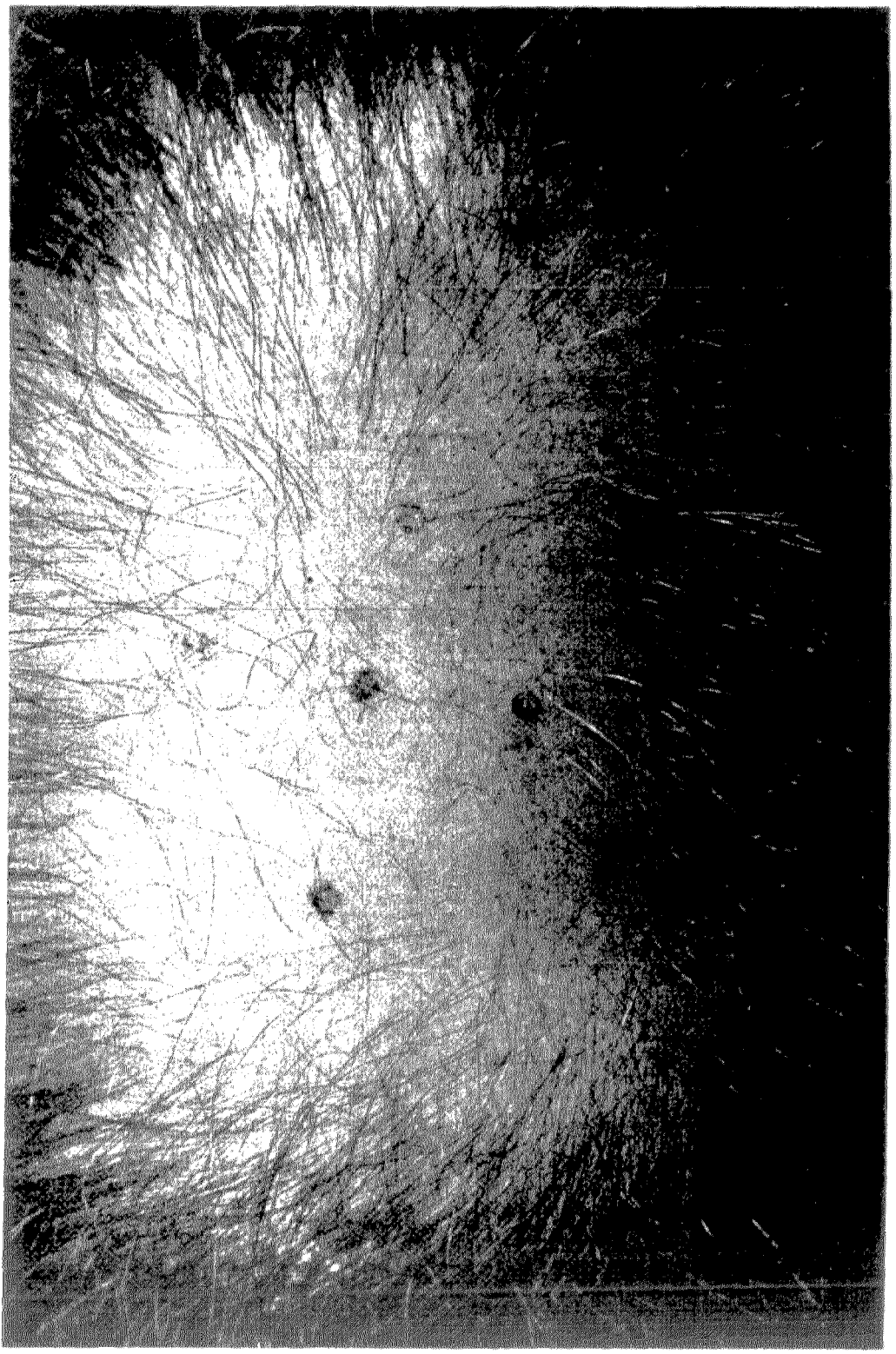
FIG. 7A to 7C are a series of photographs showing the scalp of participant 7 prior to treatment (FIG. 7A) and at months three (FIG. 7B) and six (FIG. 7C) of a six month treatment with a solution of 5% minoxidil only.
Figure 7B:
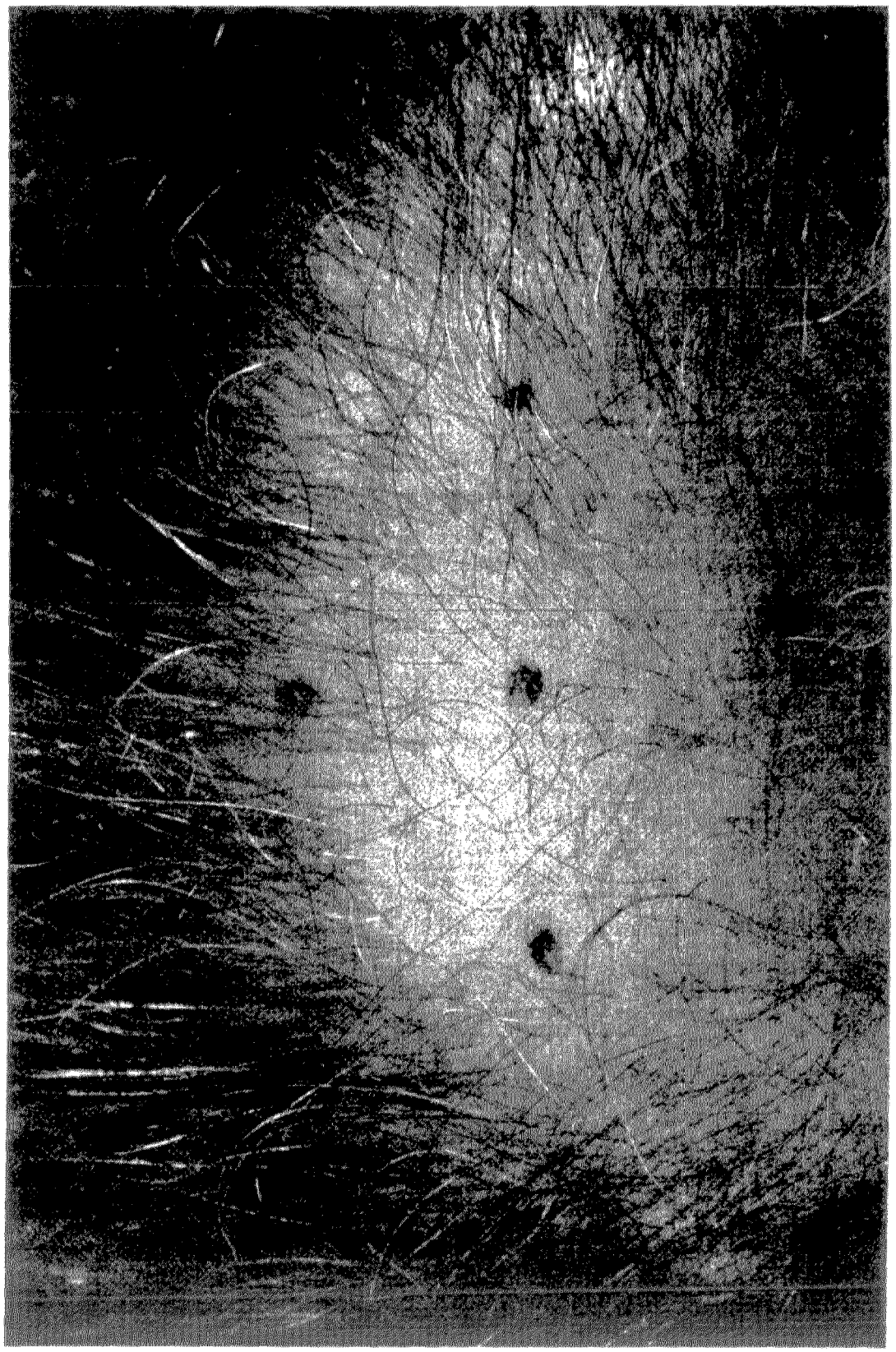
Figure 7C:
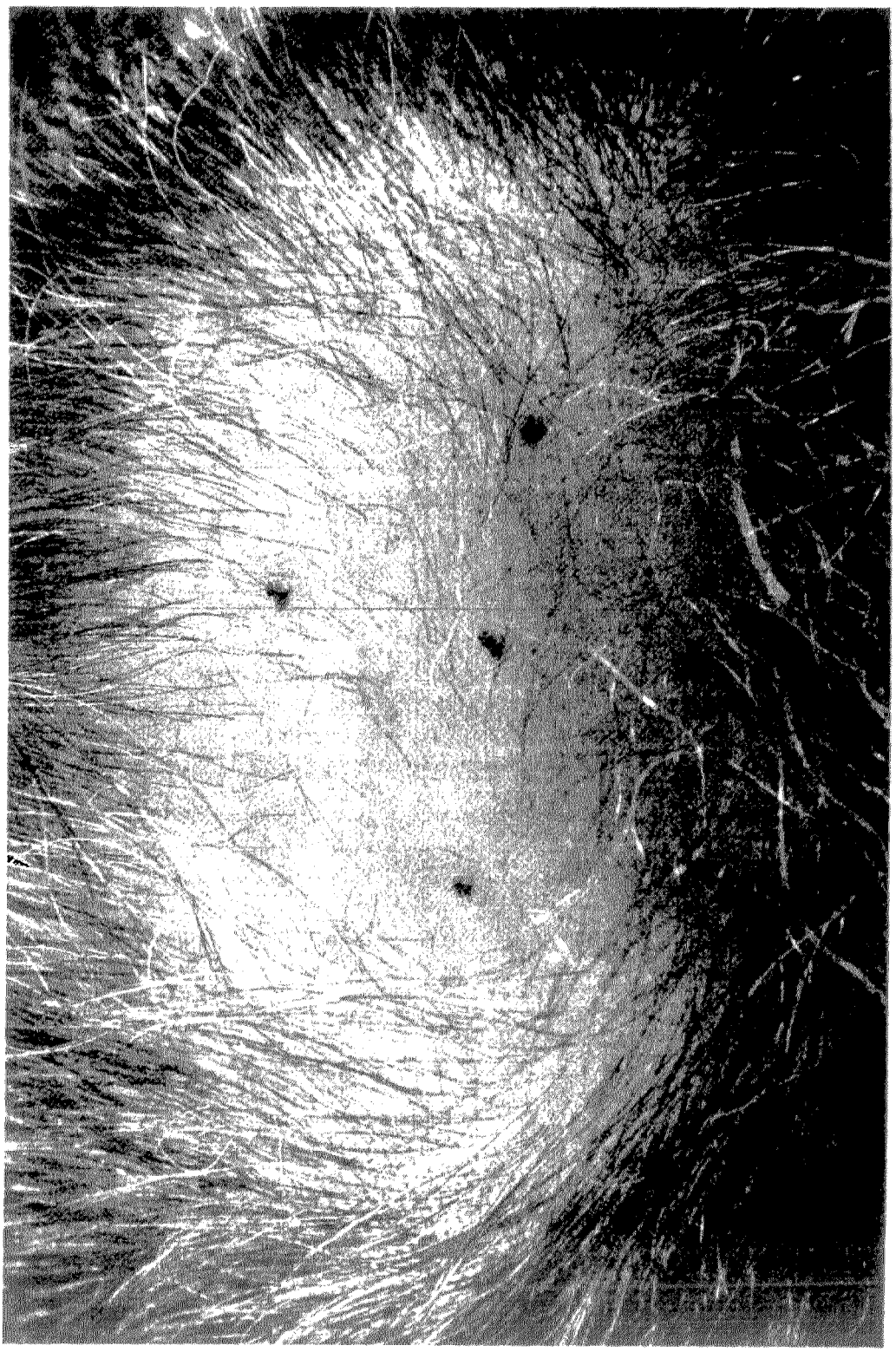
Figure 8A:
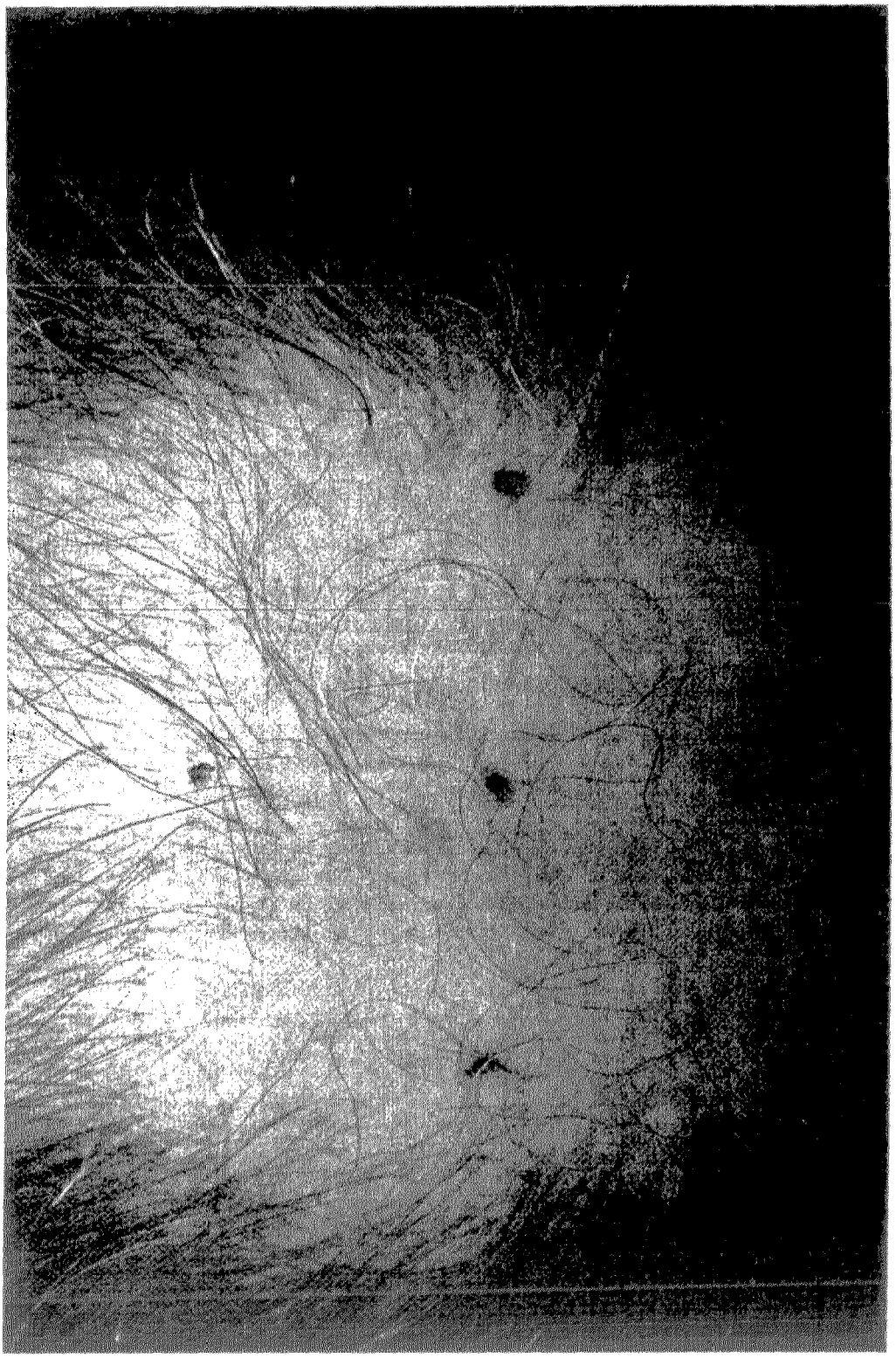
FIG. 8A to 8C are a series of photographs showing the scalp of participant 8 prior to treatment (FIG. 8A) and at months three (FIG. 8B) and six (FIG. 8C) of a six month treatment with a solution of 5% minoxidil only.
Figure 8B:
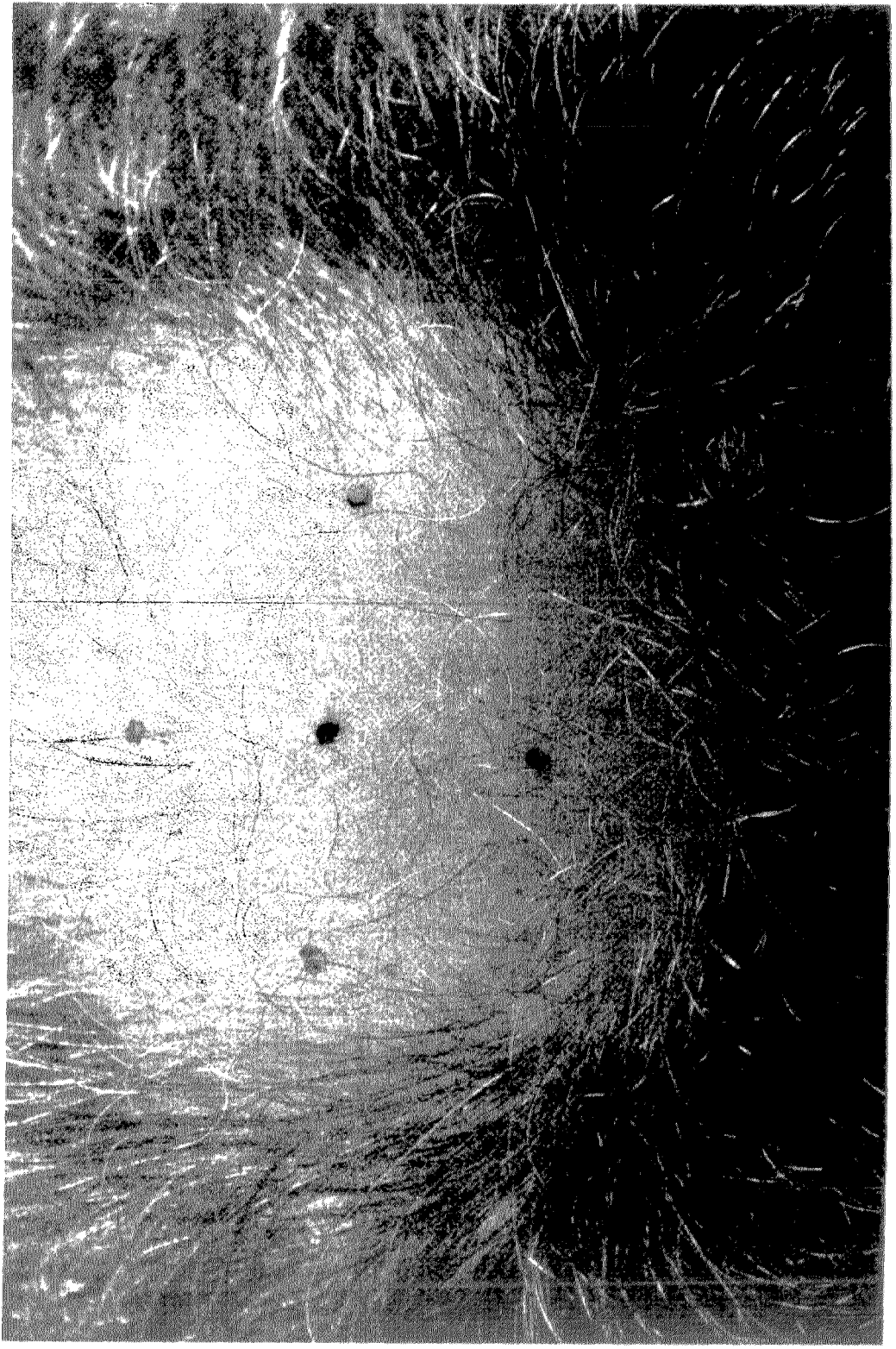
Figure 8C:
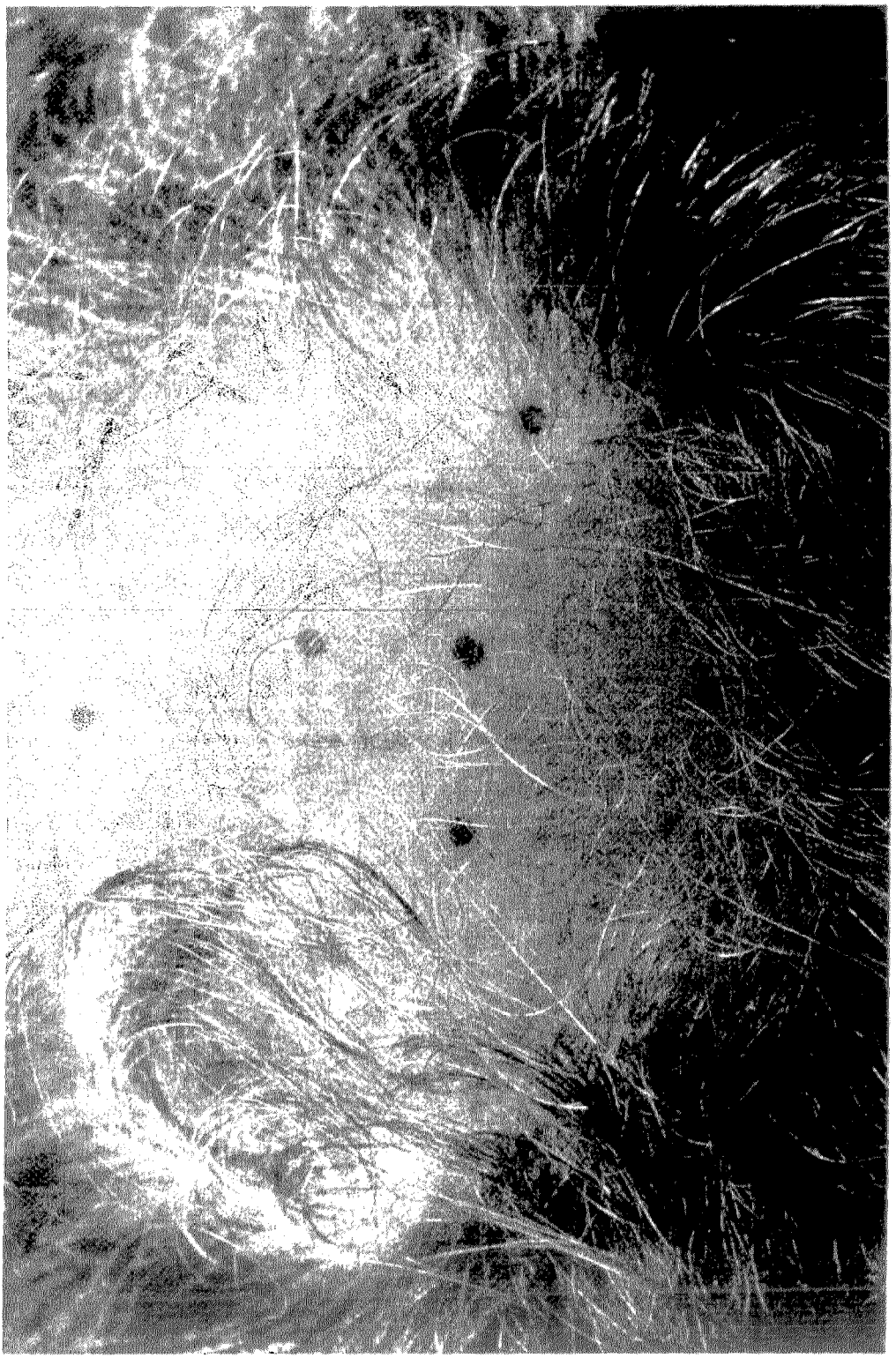
Figure 9A:
FIG. 9A to 9C are a series of photographs showing the scalp of participant 9 prior to treatment (FIG. 9A) and at months three (FIG. 9B) and six (FIG. 9C) of a six month treatment with a solution of 5% minoxidil only.
Figure 9B:
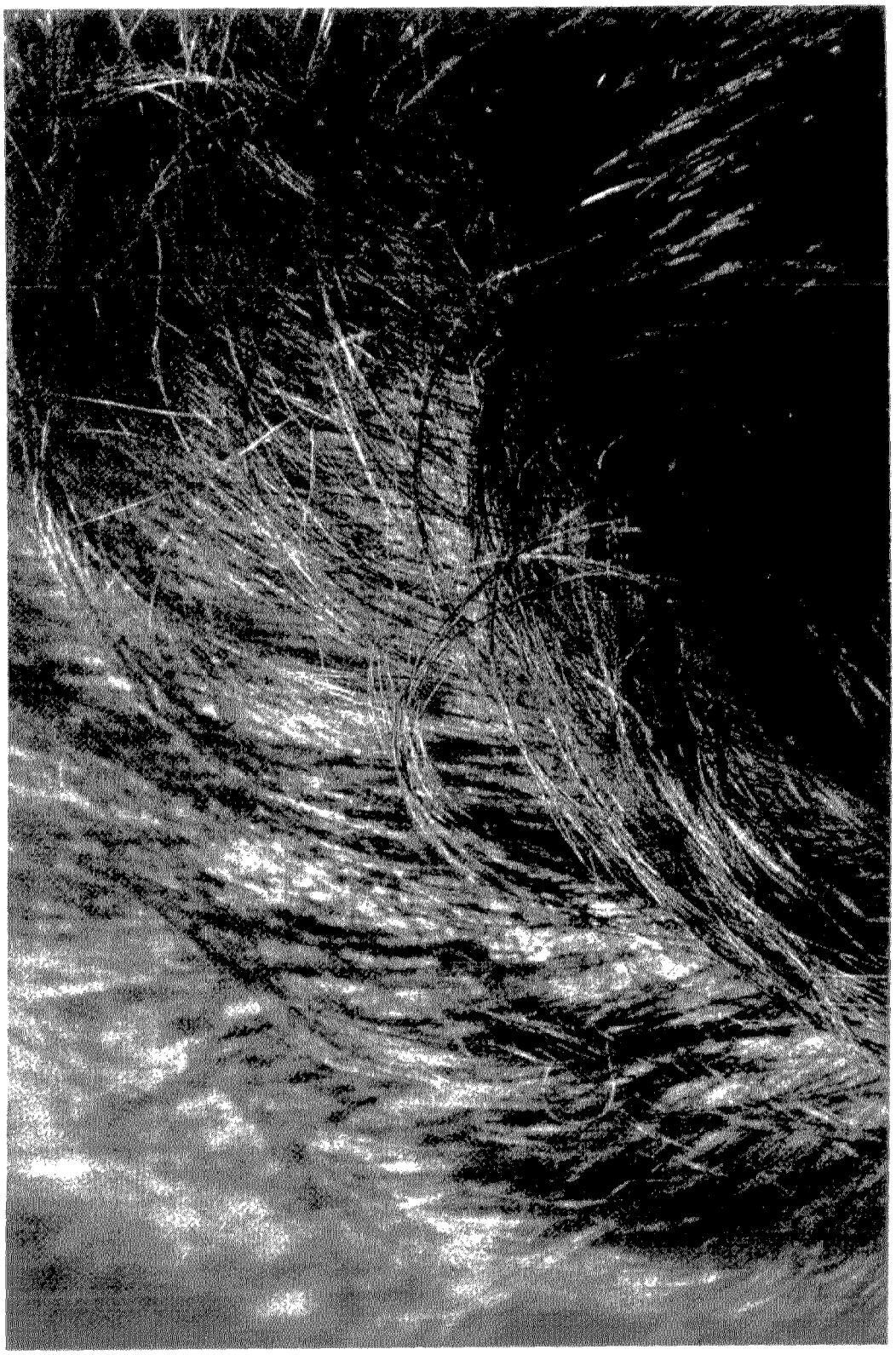
Figure 9C:
Figure 10A:
FIG. 10A to 10C are a series of photographs showing the scalp of participant 10 prior to treatment (FIG. 10A) and at months three (FIG. 10B) and six (FIG. 10C) of a six month treatment with a solution of 5% minoxidil only.
Figure 10B:
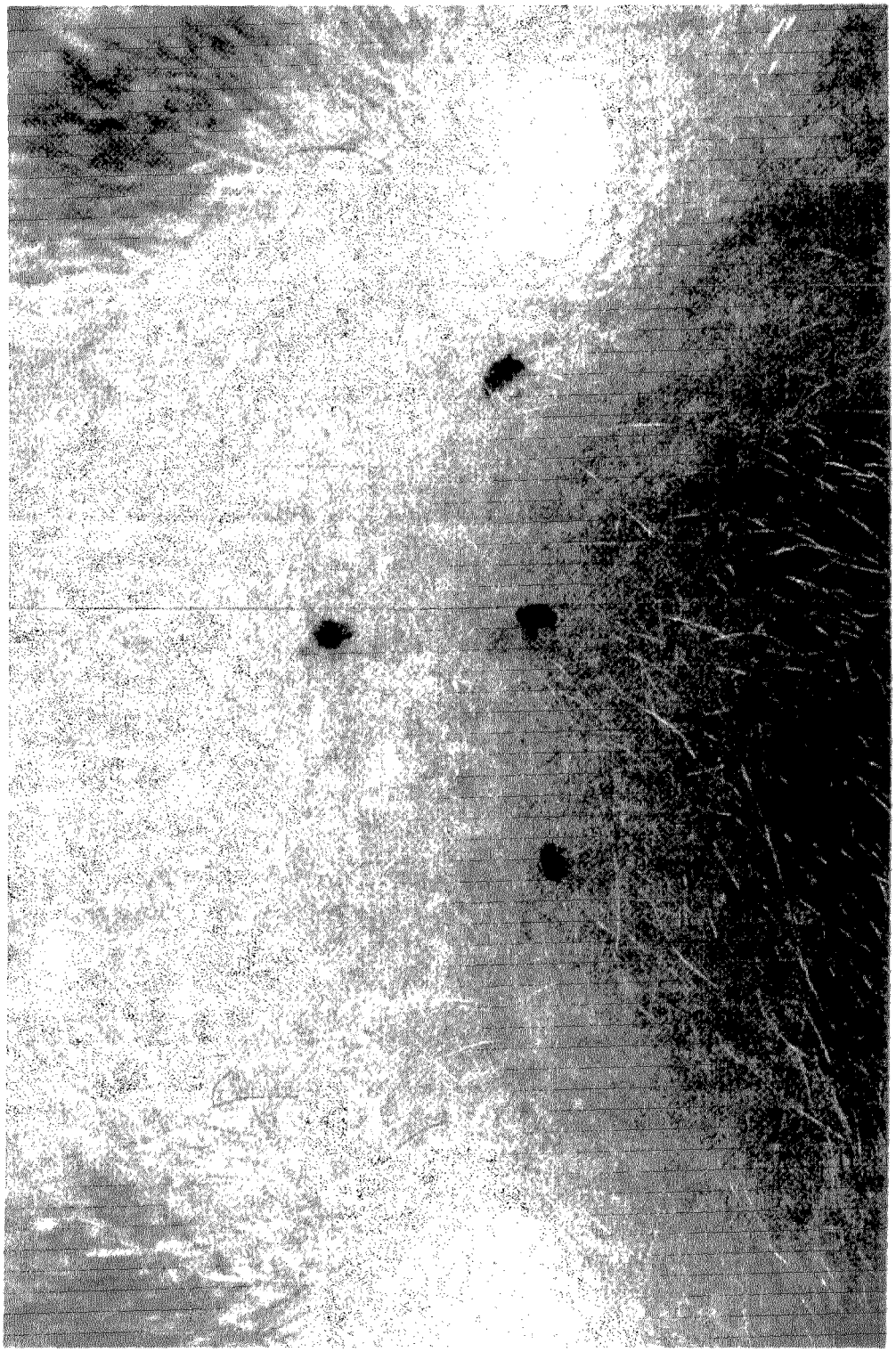
Figure 10C:
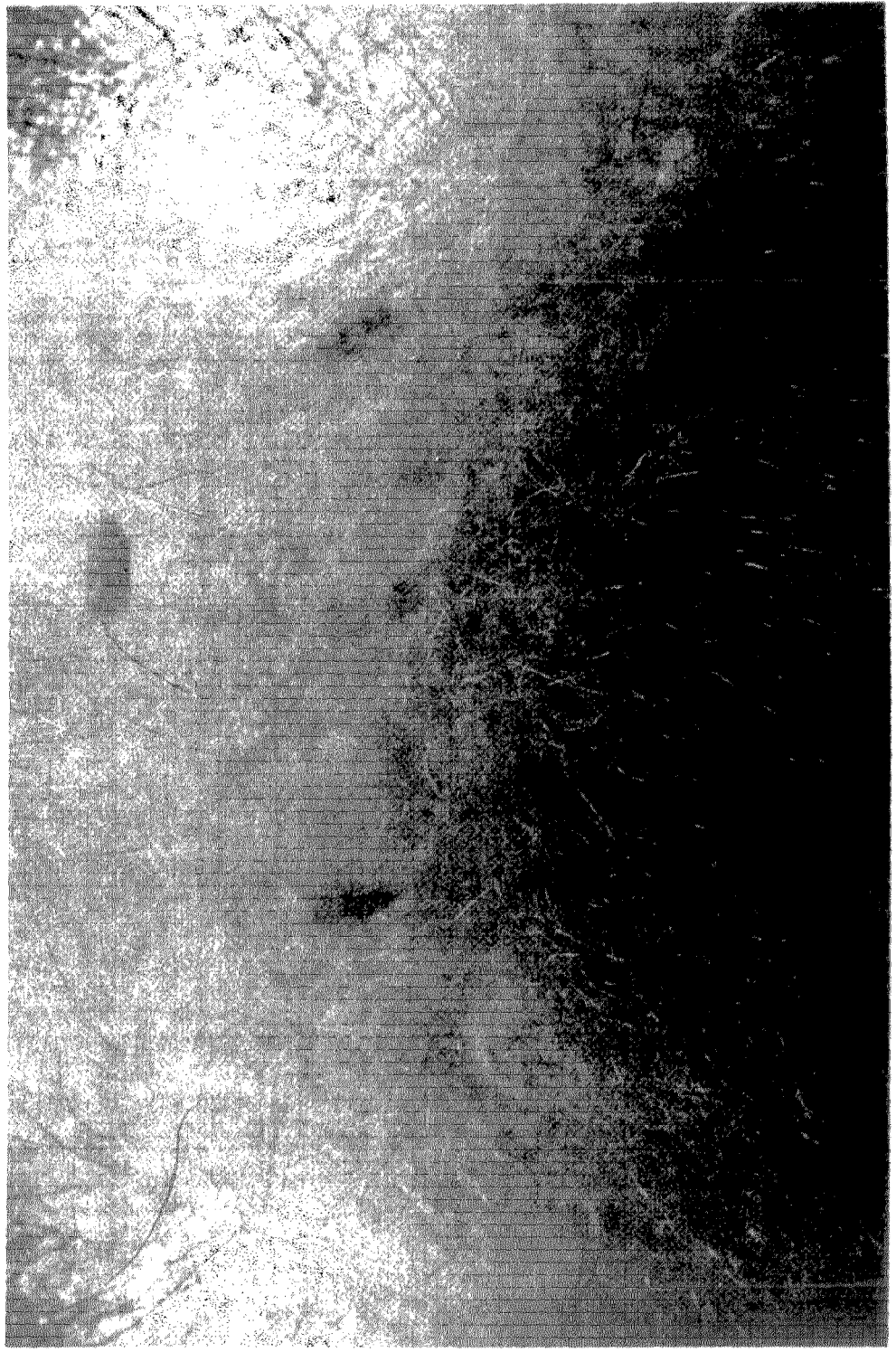
Figure 11A:
FIG. 11A to 11C are a series of photographs showing the scalp of participant 11 prior to treatment (FIG. 11A) and at months three (FIG. 11B) and six (FIG. 11C) of a six month treatment with a solution of 5% resveratrol only.
Figure 11B:
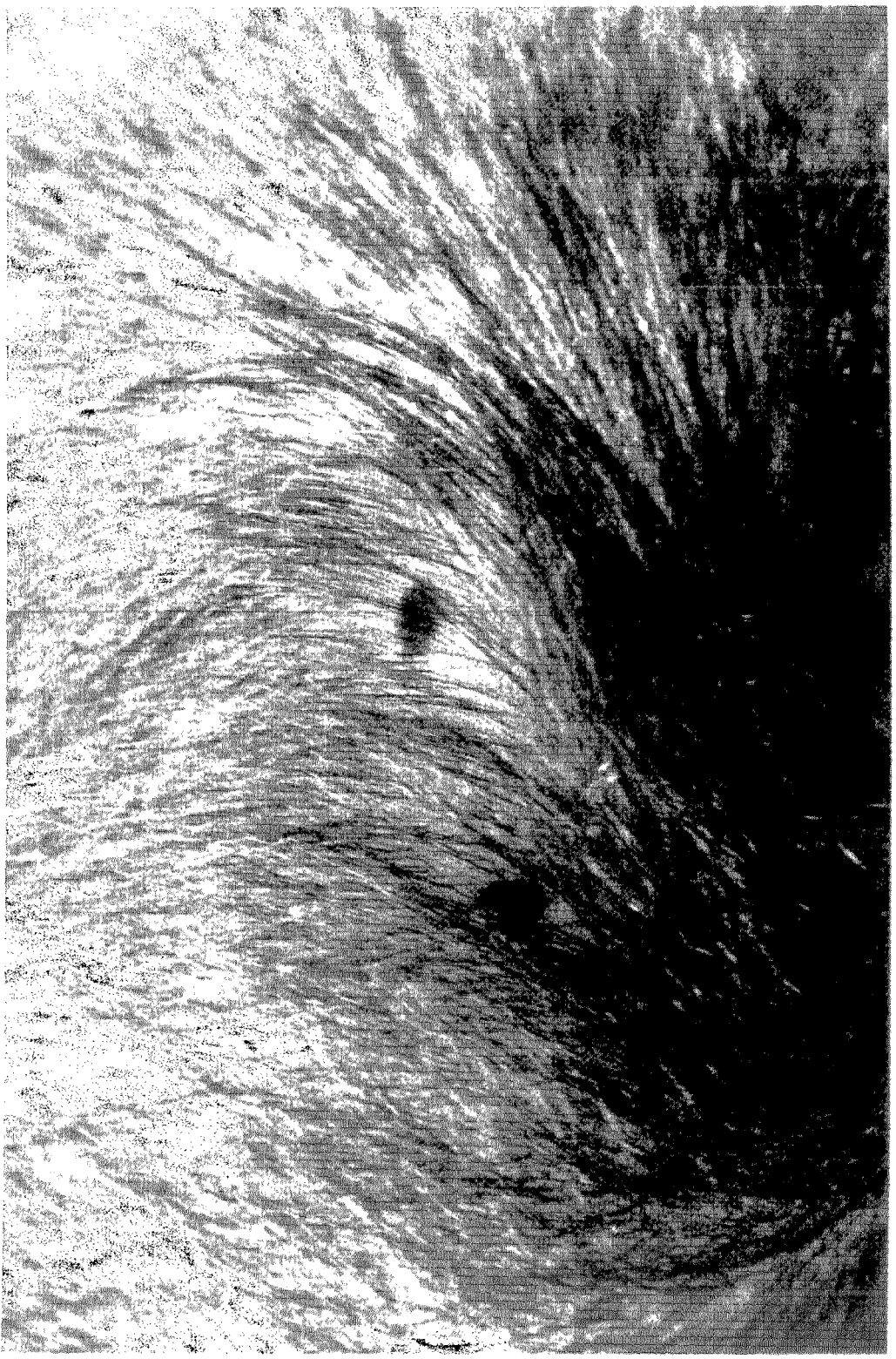
Figure 11C:
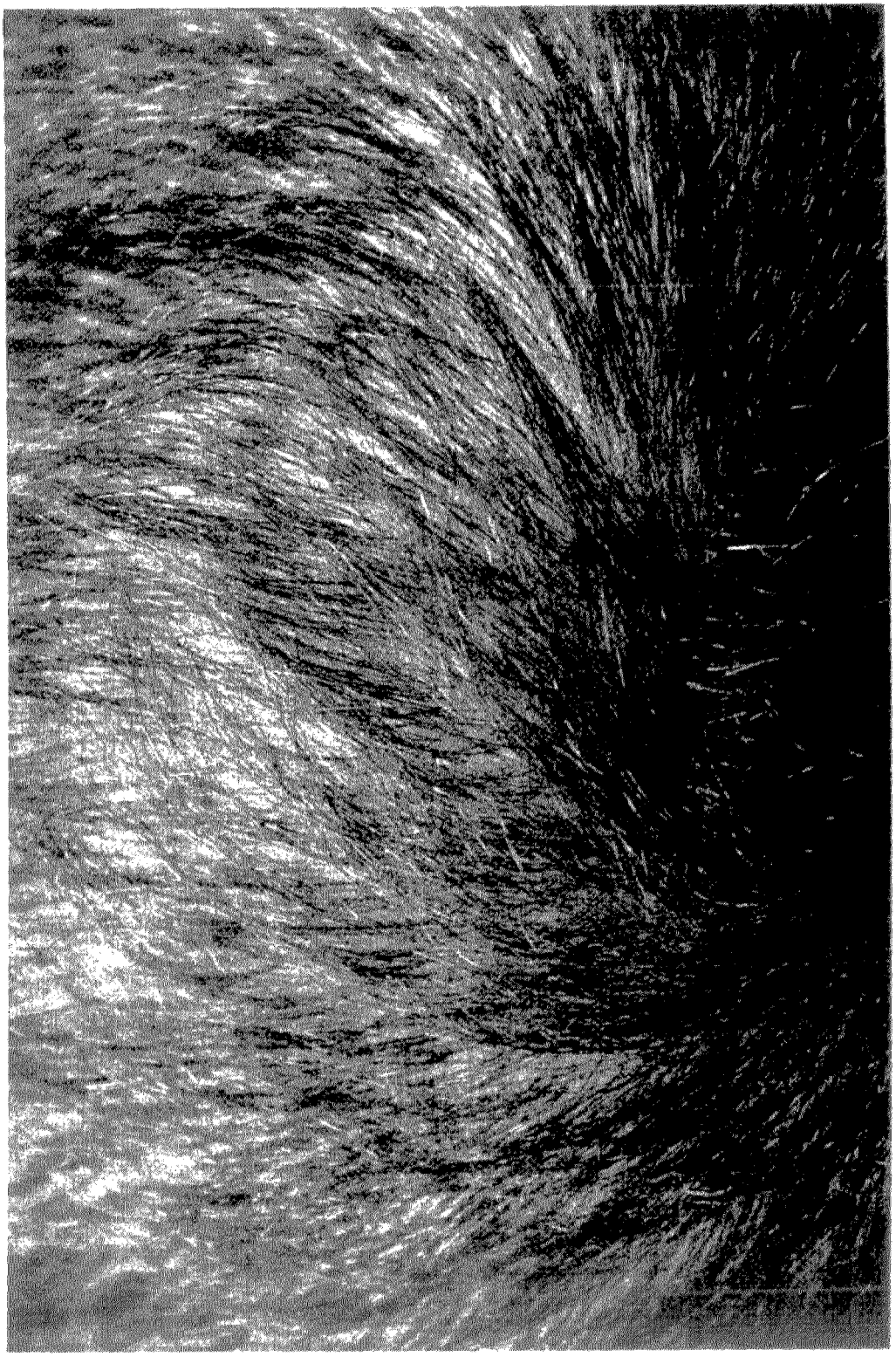
Figure 12A:
FIG. 12A to 12C are a series of photographs showing the scalp of participant 12 prior to treatment (FIG. 12A) and at months three (FIG. 12B) and six (FIG. 12C) of a six month treatment with a solution of 5% resveratrol only.
Figure 12B:
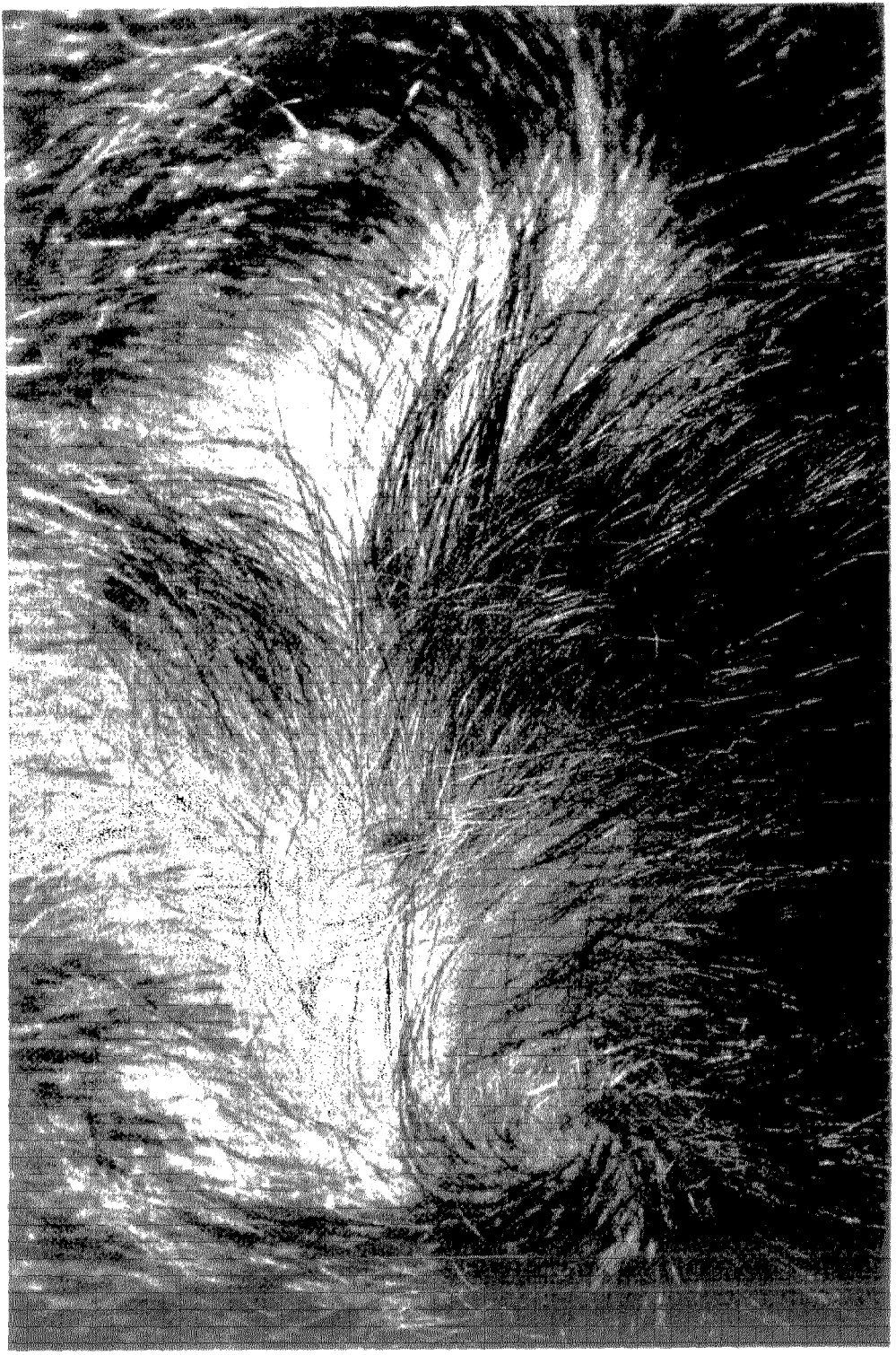
Figure 12C:
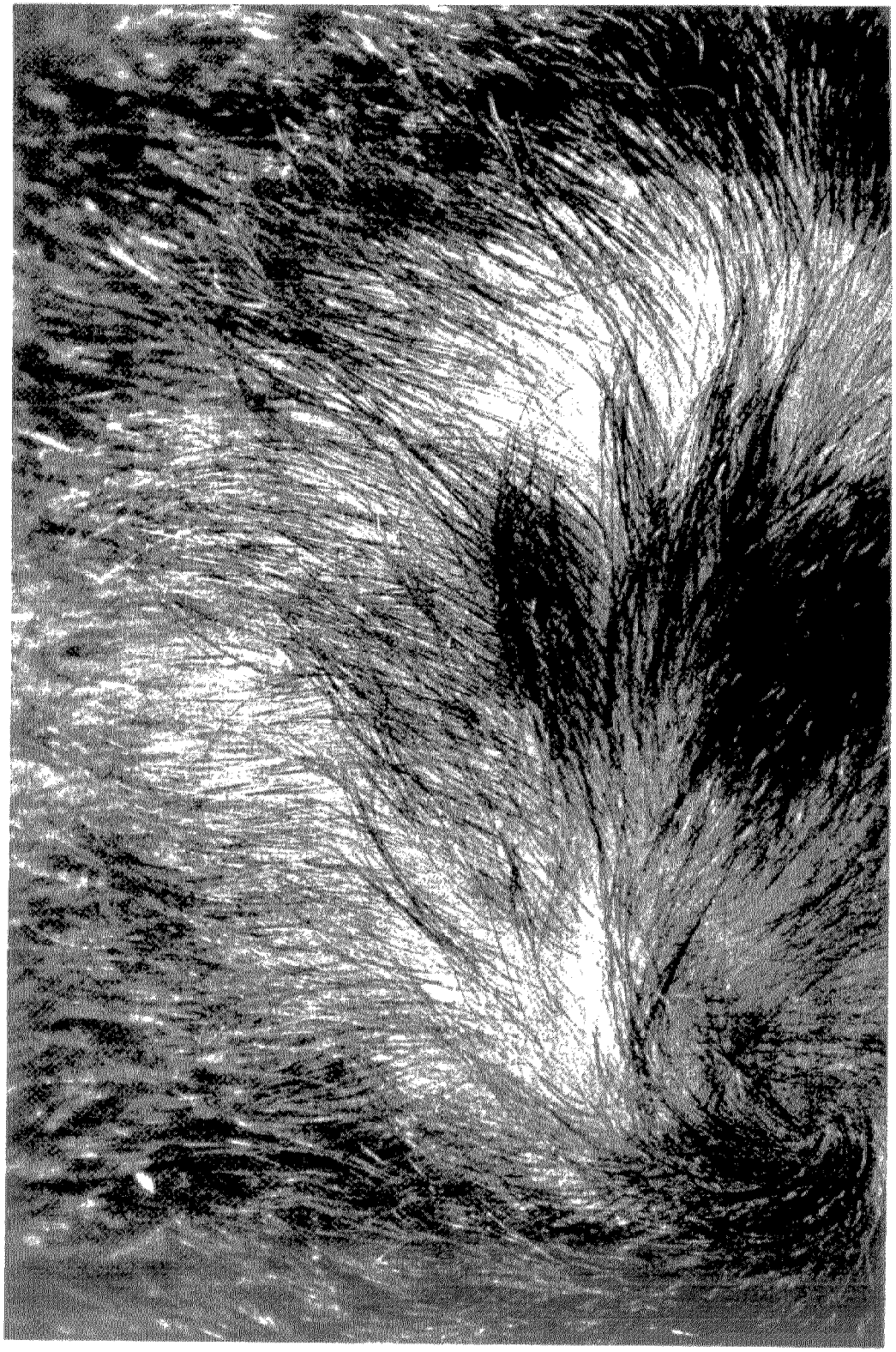
Figure 13A:
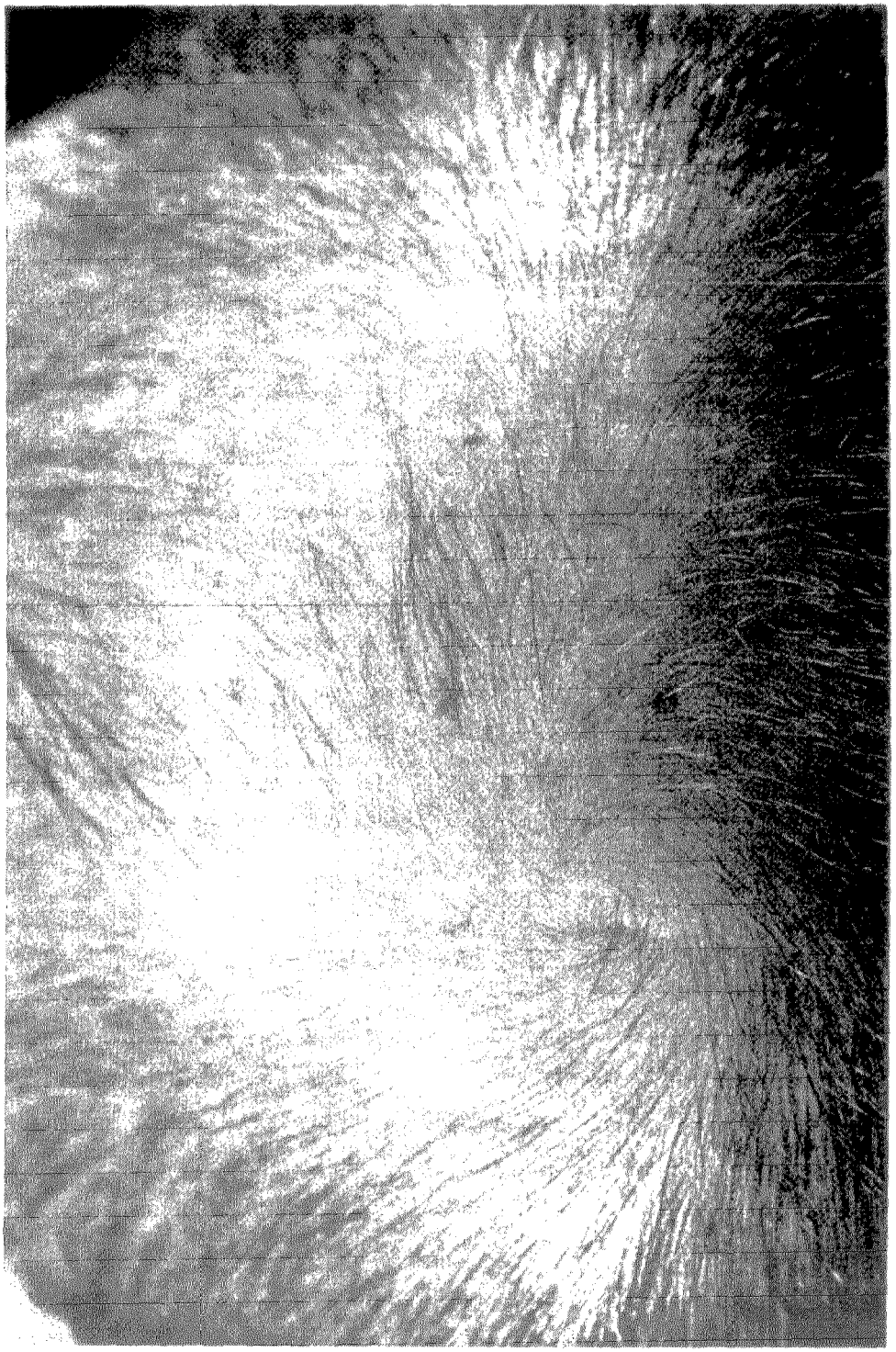
FIG. 13A to 13C are a series of photographs showing the scalp of participant 13 prior to treatment (FIG. 13A) and at months three (FIG. 13B) and six (FIG. 13C) of a six month treatment with a solution of 5% resveratrol only.
Figure 13B:
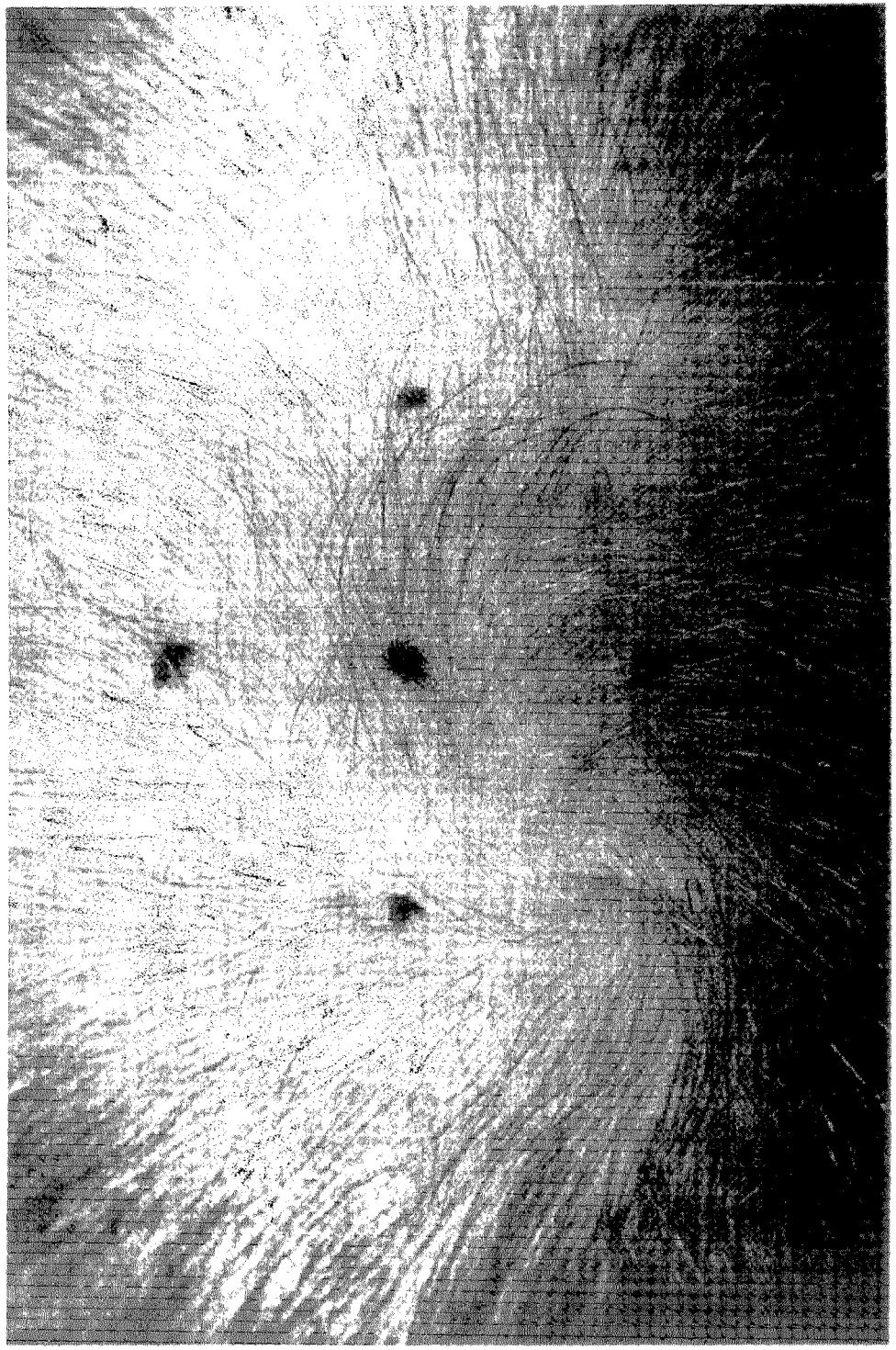
Figure 13C:
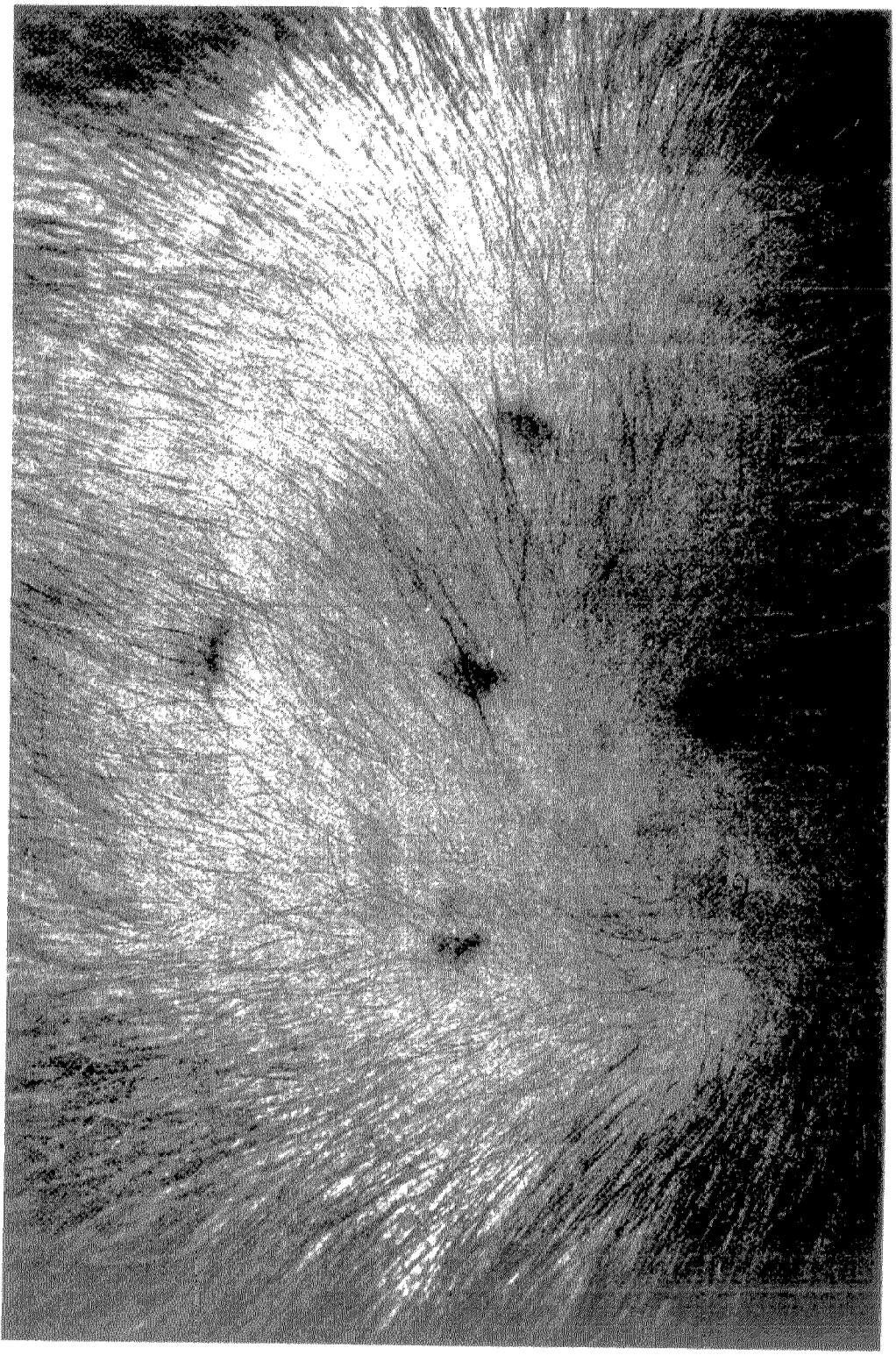
Figure 14A:
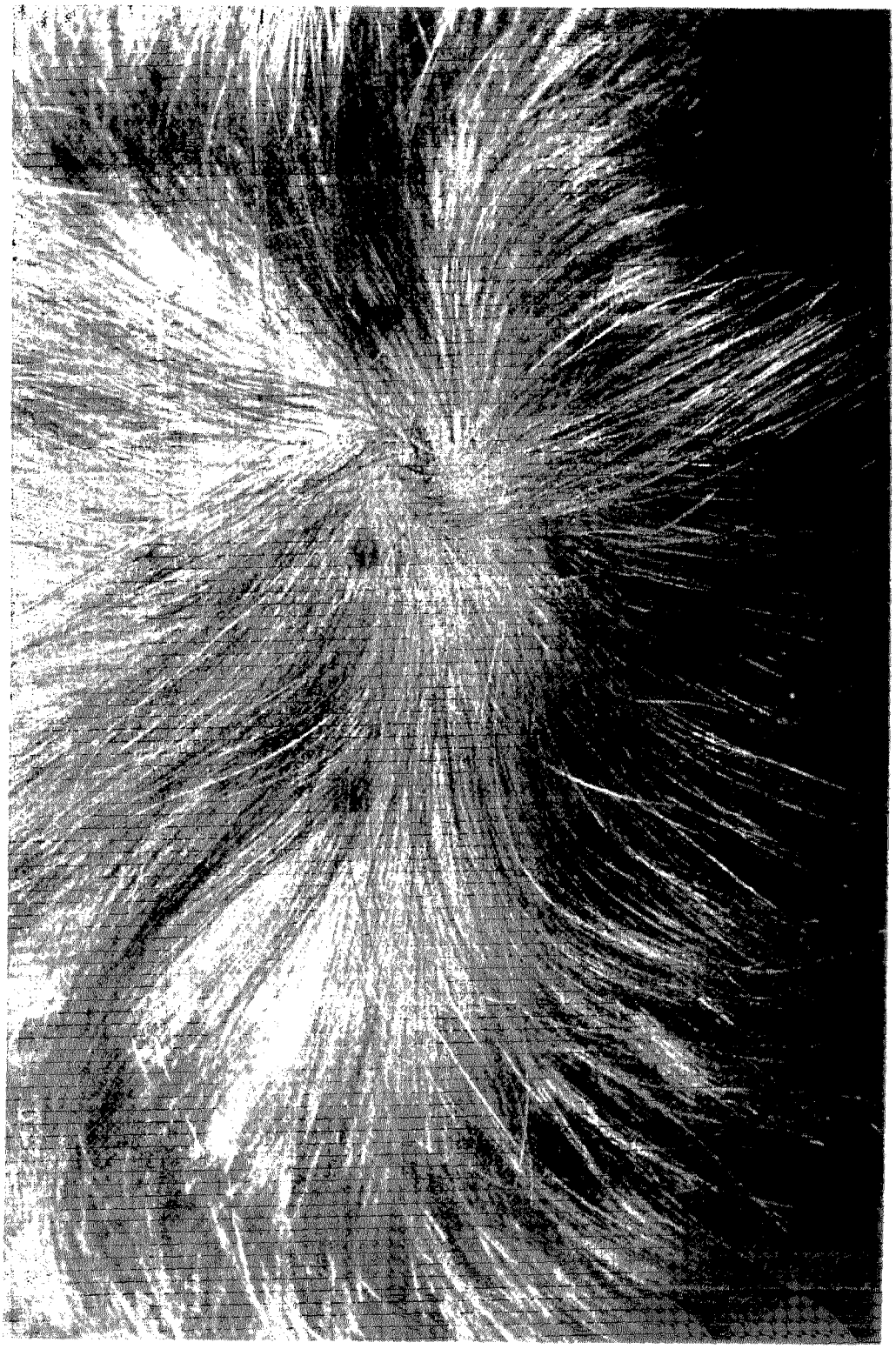
FIG. 14A to 14C are a series of photographs showing the scalp of participant 14 prior to treatment (FIG. 14A) and at months three (FIG. 14B) and six (FIG. 14C) of a six month treatment with a solution of 0.1% melatonin only.
Figure 14B:
Figure 14C:
Figure 15A:
FIG. 15A to 15C are a series of photographs showing the scalp of participant 15 prior to treatment (FIG. 15A) and at months three (FIG. 15B) and six (FIG. 15C) of a six month treatment with a solution of 0.1% melatonin only.
Figure 15B:
Figure 15C:
Figure 16A:
FIG. 16A to 16C are a series of photographs showing the scalp of participant 16 prior to treatment (FIG. 16A) and at months three (FIG. 16B) and six (FIG. 16C) of a six month treatment with a solution of 0.1% melatonin only.
Figure 16B:
Figure 16C:
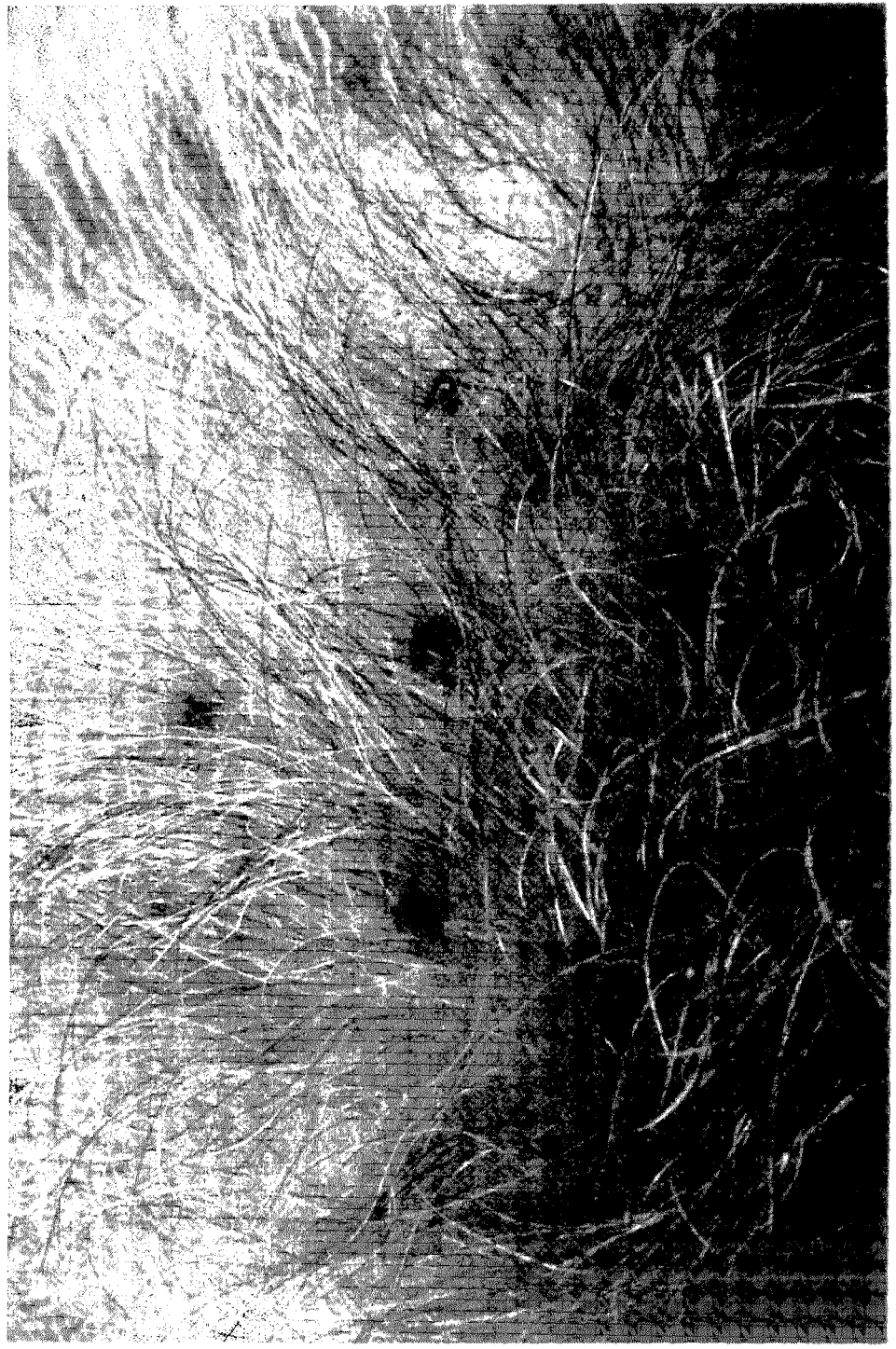
Figure 17A:
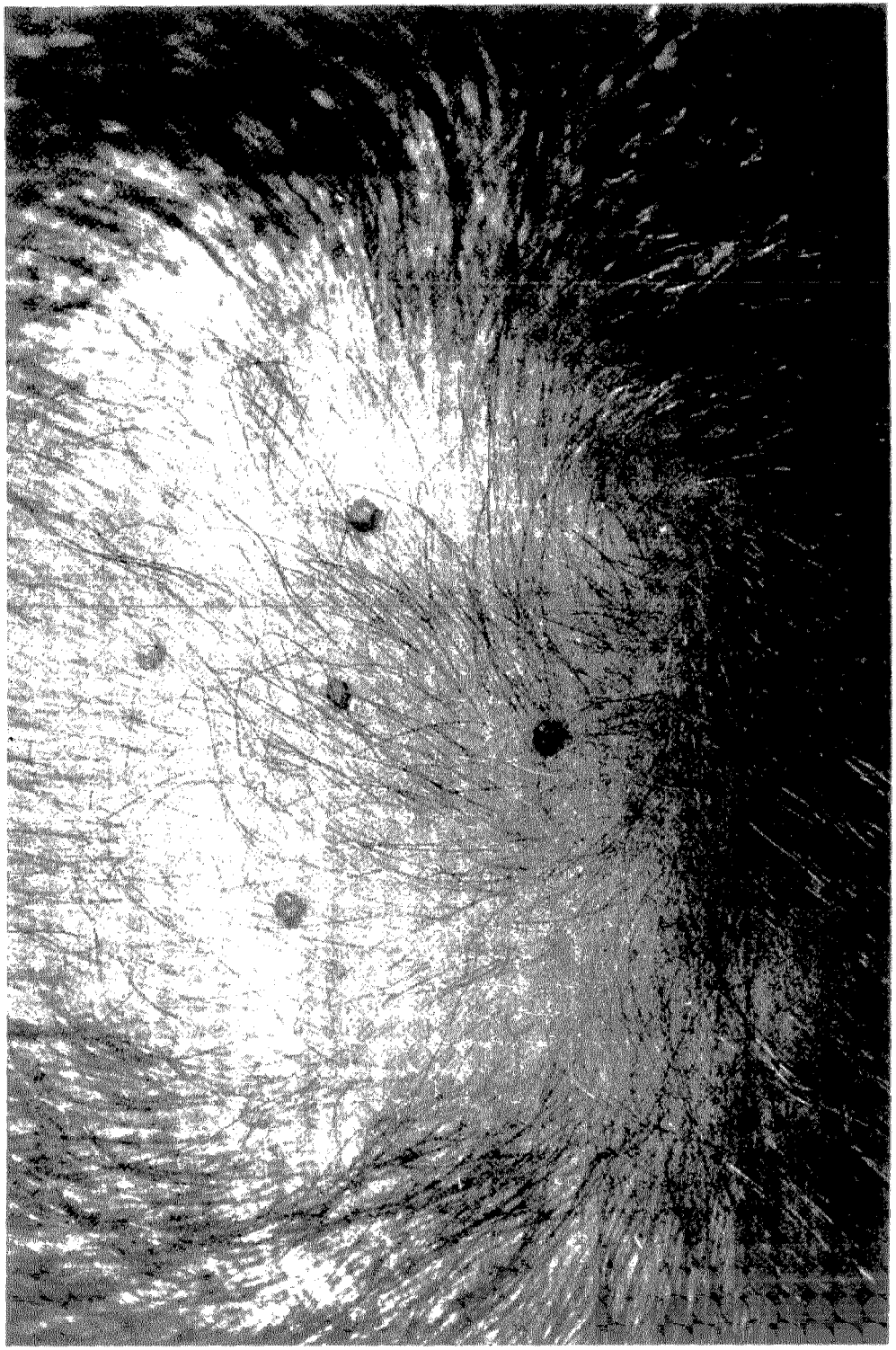
FIG. 17A to 17C are a series of photographs showing the scalp of participant 17 prior to treatment (FIG. 17A) and at months three (FIG. 17B) and six (FIG. 17C) of a six month treatment with a solution of 0.1% melatonin only.
Figure 17B:
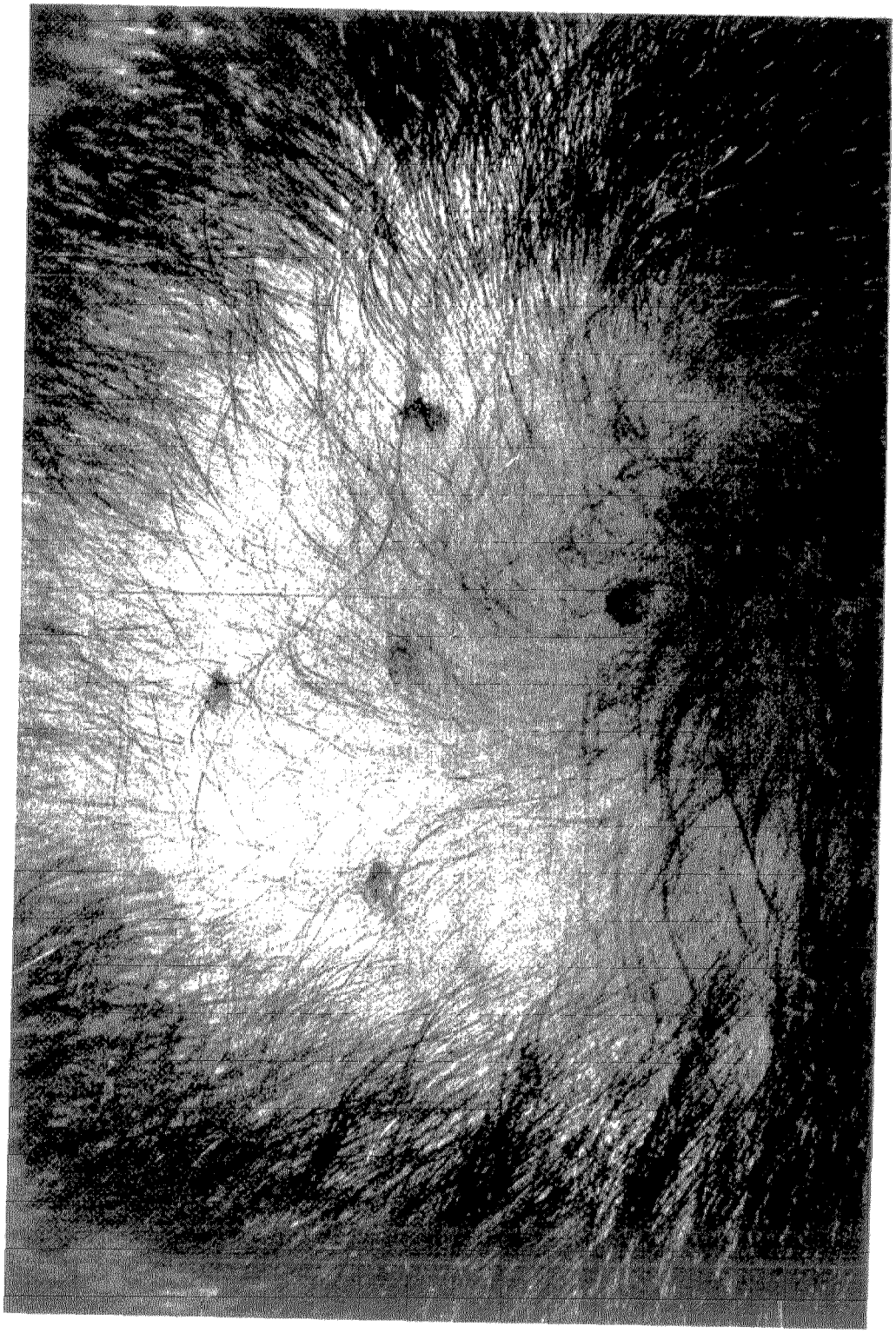
Figure 17C:
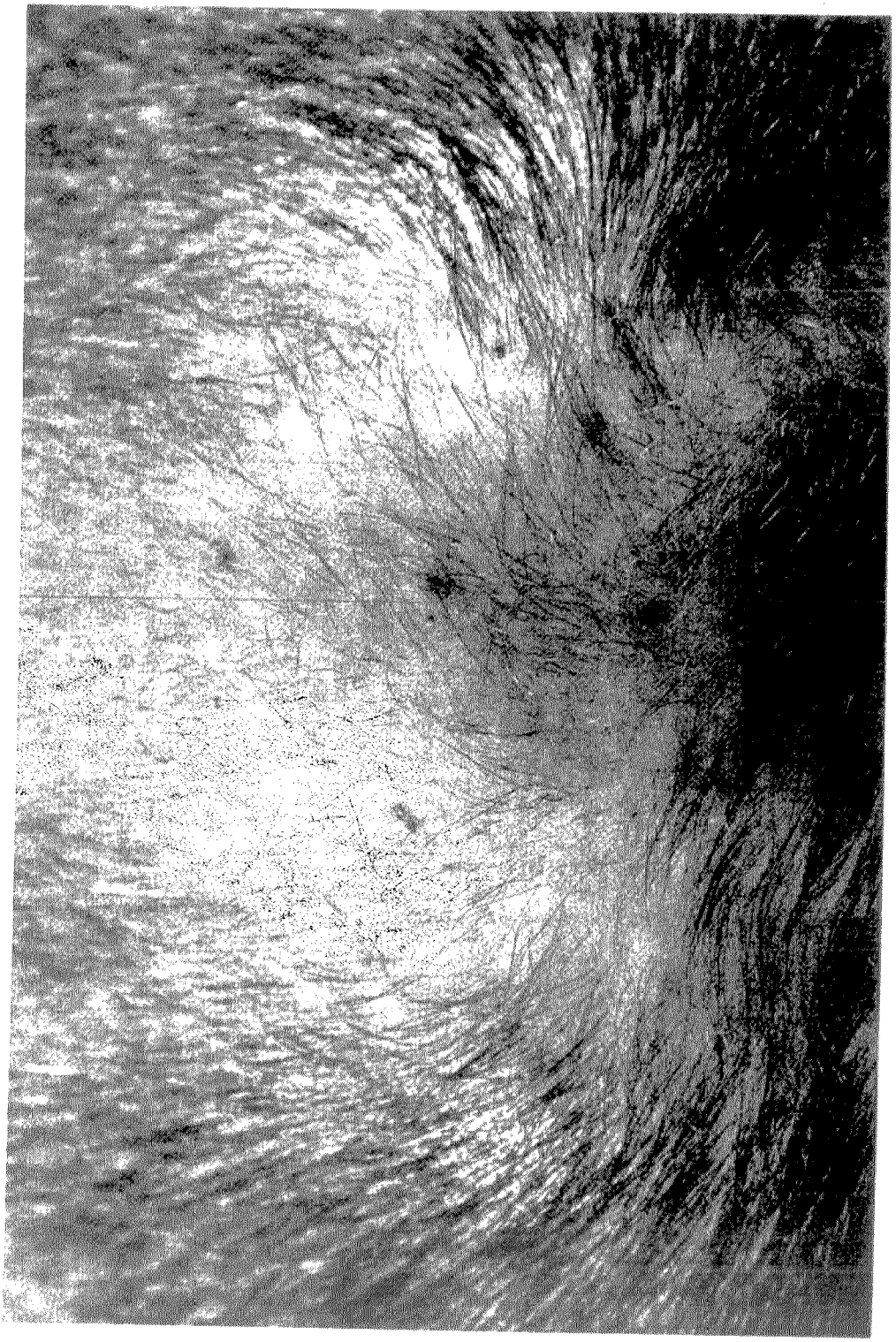
Figure 18A:
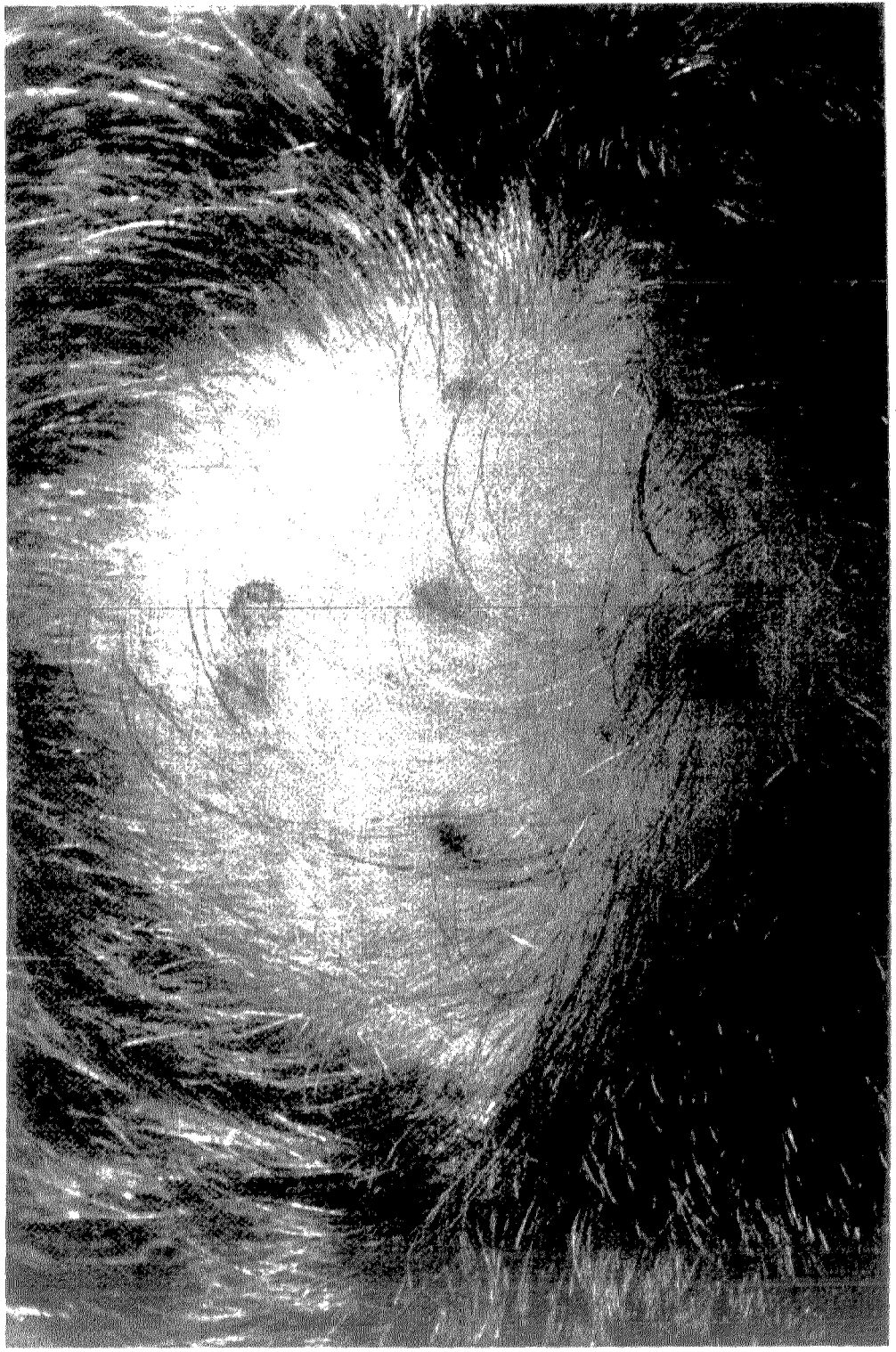
FIG. 18A to 18C are a series of photographs showing the scalp of participant 18 prior to treatment (FIG. 18A) and at months three (FIG. 18B) and six (FIG. 18C) of a six month treatment with a solution of 0.1% melatonin only.
Figure 18B:
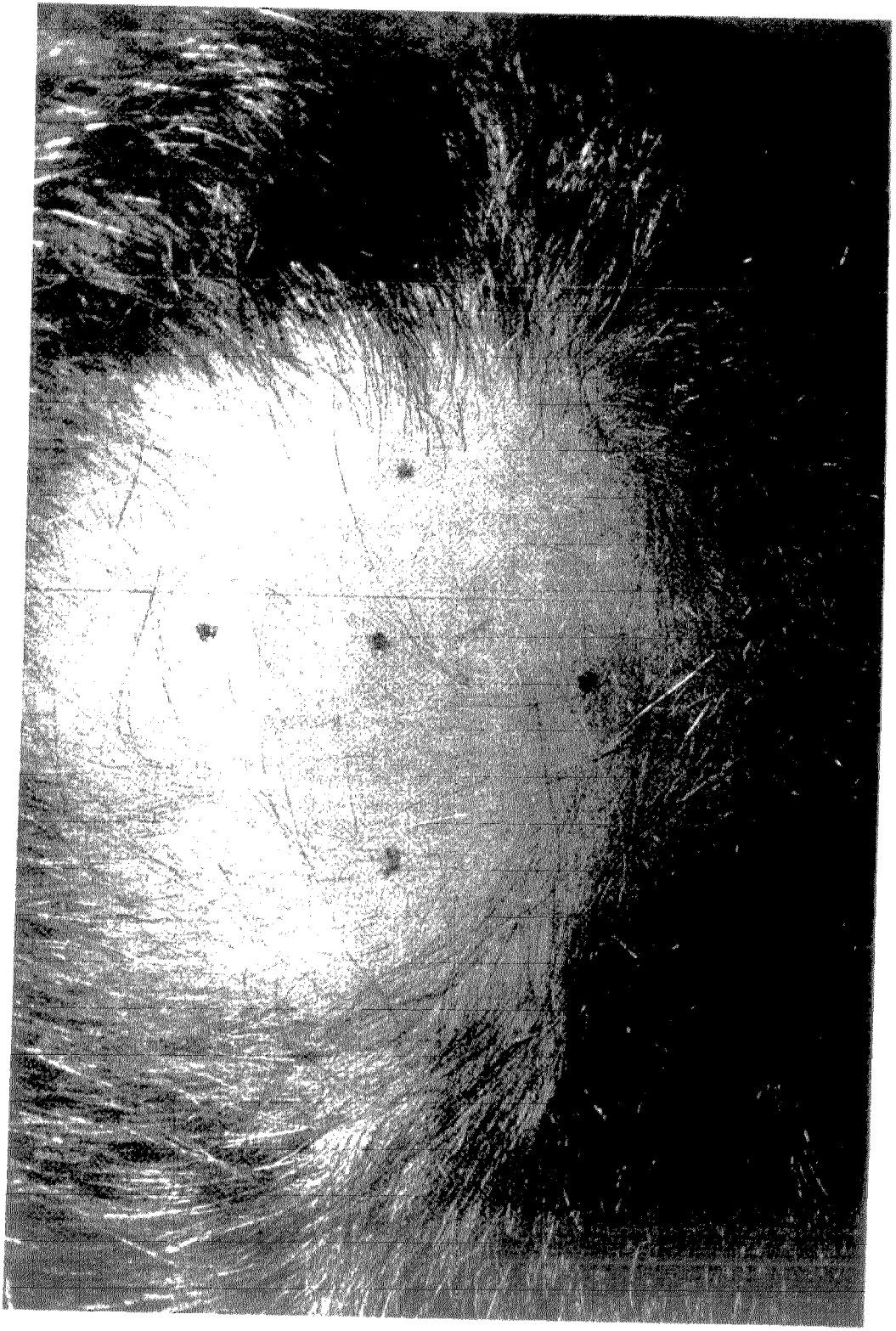
Figure 18C:
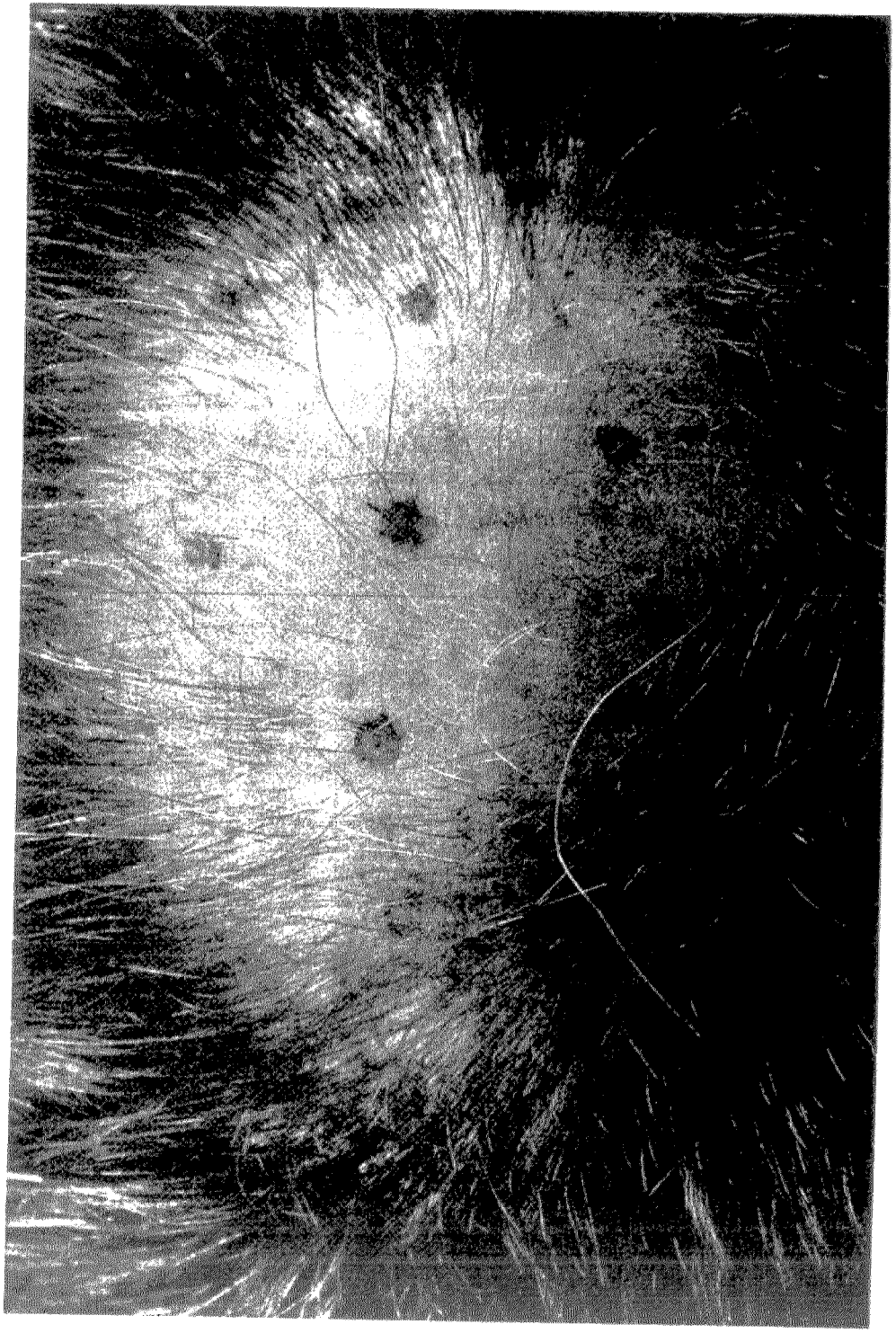

FIGS. 1 to 6 clearly show a decrease of hair loss and an increase in hair regrowth in all six participants.

Each participant completed a self-assessment questionnaire (Barber, Kaufman, Kozloff, Girman and Guess, A Hair Growth Questionnaire For Use In The Evaluation Of Therapeutic Effects In Men, Journal of Dermatological Treatment, Volume 9, Issue 3, 1998). All participants agreed that they could see their bald spot getting smaller after receiving treatment. 84% of the participants saw an improvement in the appearance of their hair. 83% of the participants saw a slight to moderate increase in the growth of their hair while all participants found that the treatment had been somewhat to very effective at slowing down hair loss.

A marked decrease of hair loss and an increase in hair regrowth was observed for each participant.

B. Comparison with Treatment with Minoxidil, Resveratrol and Melatonin

Each participant first had his hair analysed as described in part A above. Following the first analysis, each participant was provided with a solution comprising either 5% minoxidil, 5% resveratrol, or 0.1% melatonin. The compositions were prepared as described in Examples 2 to 4 above. The participants applied 1 ml to the scalp, once a day after cleansing. The 1 ml was applied as 10 metered dose sprays of 0.1 ml.

a) 5% Minoxidil Comparator

Four participants were provided with a solution of 5% minoxidil. The particulars of the participant are provided in Table 2 below.

TABLE 2

| Participant | Gender | Age |
|---|---|---|
| 7 | Male | 64 |
| 8 | Male | 45 |
| 9 | Male | 52 |
| 10 | Male | 48 |

Only a slight improvement in hair regrowth is observed for the minoxidil group and the results are inferior to those seen with the composition of the invention.

The four participants completed the self-assessment questionnaire described above. Half of the participants agreed that their bald spot decreased in size and that the appearance of their hair was a little better. 75% of the participants saw a little increase in the growth of their hair and found the treatment somewhat effective in slowing down hair loss.

b) 5% Resveratrol Comparator

Three participants were provided with a solution of 5% resveratrol. Particulars of the participants are provided in the Table 3 below.

TABLE 3

| Participant | Gender | Age |
|---|---|---|
| 11 | Male | 38 |
| 12 | Male | 31 |
| 13 | Male | 42 |

Only a slight improvement in hair regrowth is observed for the resveratrol only group. The results are inferior to those seen with the composition of the invention.

Two of the participants disagreed that their bald spot had gotten smaller and the other participants had no opinion. Two of the participants thought that the appearance of their hair was the same as before treatment and one thought that it was worse. All participants saw a slight increase in the growth of their hair. Two out of the three participants thought that the treatment was somewhat effective at slowing down hair loss while the other participant thought it was not very effective.

c) 0.1% Melatonin Comparator

Five participants were provided with a solution of 0.1% melatonin only. The particulars of these participants are provided in Table 4 below.

TABLE 4

| Participant | Gender | Age |
|---|---|---|
| 14 | Male | 35 |
| 15 | Female | 36 |
| 16 | Male | 45 |
| 17 | Male | 42 |
| 18 | Male | 40 |

Only a slight improvement in hair regrowth was observed for the melatonin only group. The results obtained are inferior to those observed with the composition of the invention.

The self-assessment questionnaire reflected the fact that 80% of the participants either disagreed or strongly disagreed that their bald spot had gotten smaller and the remaining 20% had no opinion. 60% of the participants were of the view that the appearance of the hair remained unchanged, 20% believed it had gotten worse while 20% thought it was a little better. 80% of the participants saw no change in the growth of their hair while 20% saw a slight increase. 80% of the participants were of the view that the treatment was not very affective at slowing down hair loss and 20% thought it was not effective at all.

The composition comprising resveratrol and melatonin shows improved properties in terms of reduction of hair loss and increase of regrowth of hair when compared to a solution of 5% minoxidil alone, a solution of 5% resveratrol alone or a solution of 0.1% melatonin alone. The improvements shown in the reduction of hair loss and the increase of regrowth hair for the composition of the invention are superior to the improvements seen for each of the components of the composition taken individually and the results obtained to date suggest that the improvements may be superior to those of the sum of the said components.

While the composition of the invention has been tested on males, similar results are expected on females as the mechanism of hair growth is the same for both genders.

While the present invention has been described in connection with specific embodiments thereof and in a specific use, various modifications will occur to those skilled in the art. The scope of the claims should not be limited by the preferred embodiments or the examples but should be given the broadest interpretation consistent with the description as a whole.

What is claimed is:

1. A composition comprising 0.01% to 15% of resveratrol and 0.01% to 15% of melatonin for use in reducing hair loss, in increasing regrowth of hair, or in reducing hair loss and increasing regrowth of hair in a human subject.

2. The composition according to claim 1 comprising 5% of resveratrol and 0.01% of melatonin.

3. The composition of claim 1, wherein the human subject is a male.

4. The composition of claim 1, wherein the human subject is a female.

5. The composition of claim 1 for topical administration.

6. The composition according to claim 1 which is in the form of a spray.

7. A method to reduce hair loss, increase regrowth of hair, or reduce hair loss and increase regrowth of hair in a human subject, comprising applying a composition comprising 0.01% to 15% of resveratrol and 0.01% to 15% of melatonin to a scalp of a human subject.

8. The method according to claim 7, wherein the human subject is a male.

9. The method according to claim 7, wherein the human subject is a female.

10. The method according to claim 7, wherein the composition is applied to the scalp in the form of a spray.

11. A method to reduce hair loss, increase regrowth of hair, or reduce hair loss and increase regrowth of hair in a human subject, comprising applying a composition comprising 5% of resveratrol and 0.01% of melatonin to a scalp of a human subject.

12. The method according to claim 11, wherein the human subject is a male.

13. The method according to claim 11, wherein the human subject is a female.

14. The method according to claim 11, wherein the composition is applied to the scalp in the form of a spray.

* * * * *